US010780154B2

(12) United States Patent
Wu et al.

(10) Patent No.: US 10,780,154 B2
(45) Date of Patent: Sep. 22, 2020

(54) *SALMONELLA PARATYPHI A* WITH AN O-ANTIGEN HAVING AN EXTENDED CARBOHYDRATE CHAIN AND USE THEREOF

(71) Applicant: Institute of Biotechnology, Academy of Military Medical Sciences, China, Beijing (CN)

(72) Inventors: Jun Wu, Beijing (CN); Hengliang Wang, Beijing (CN); Peng Sun, Beijing (CN); Bo Liu, Beijing (CN); Li Zhu, Beijing (CN); Chao Pan, Beijing (CN); Tiantian Wang, Beijing (CN); Xin Gong, Beijing (CN); Shaohong Chang, Beijing (CN); Erling Feng, Beijing (CN)

(73) Assignee: Institute of Biotechnology, Academy of Military Medical Sciences, China, Beijing (CN)

( * ) Notice: Subject to any disclaimer, the term of this patent is extended or adjusted under 35 U.S.C. 154(b) by 0 days.

(21) Appl. No.: 15/532,823

(22) PCT Filed: Sep. 7, 2015

(86) PCT No.: PCT/CN2015/089045
§ 371 (c)(1),
(2) Date: Jun. 2, 2017

(87) PCT Pub. No.: WO2016/090980
PCT Pub. Date: Jun. 16, 2016

(65) Prior Publication Data

US 2018/0050100 A1 Feb. 22, 2018

(30) Foreign Application Priority Data

Dec. 8, 2014 (CN) .......................... 2014 1 0743690

(51) Int. Cl.

| | |
|---|---|
| ***A61K 39/02*** | (2006.01) |
| ***A61K 39/112*** | (2006.01) |
| ***C12N 15/63*** | (2006.01) |
| ***A61K 48/00*** | (2006.01) |
| ***C12N 15/11*** | (2006.01) |
| ***C12N 9/10*** | (2006.01) |
| ***C12N 9/00*** | (2006.01) |
| ***C12N 15/74*** | (2006.01) |
| ***A61K 39/00*** | (2006.01) |

(52) U.S. Cl.
CPC .......... *A61K 39/0275* (2013.01); *A61K 48/00* (2013.01); *C12N 9/1051* (2013.01); *C12N 9/93* (2013.01); *C12N 15/11* (2013.01); *C12N 15/63* (2013.01); *C12N 15/74* (2013.01); *C12Y 204/01* (2013.01); *C12Y 600/00* (2013.01); *A61K 2039/521* (2013.01); *A61K 2039/523* (2013.01)

(58) Field of Classification Search
None
See application file for complete search history.

(56) References Cited

FOREIGN PATENT DOCUMENTS

| | | | | | |
|---|---|---|---|---|---|
| CN | 1448504 | A | 10/2003 | | |
| CN | 101983070 | A | 3/2011 | | |
| CN | 102140430 | A | 8/2011 | | |
| CN | 102935226 | A | 2/2013 | | |
| EP | 3 225 690 | A1 | 10/2017 | | |
| WO | WO 2009/104074 | A2 | 8/2009 | | |
| WO | 2010101750 | * | 10/2010 | .......... | A61K 39/112 |
| WO | 20104043637 | * | 3/2014 | .............. | C12N 1/21 |

OTHER PUBLICATIONS

Stevenson et al. FEMS Microbiology Letters vol. 125, pp. 23-30, 1995 (Year: 1995).*
McClelland et al. Nature, vol. 413, Oct. 2001. (Year: 2001).*
Bastin et al. Molecular Microbiology vol. 7 No. 5 pp. 725-734 1993 (Year: 1993).*
International Search Report (ISR) for PCT/CN2015/089045; I.A. fd: Sep. 7, 2015, dated Dec. 15, 2015, State Intellectual Property Office of the P.R. China, Beijing, China.
International Preliminary Report on Patentability (IPRP) including the Written Opinion of the International Searching Authority (PCT Rule 44bis) for PCT/CN2015/089045; I.A. fd: Sep. 7, 2015, dated Jun. 13, 3017, by the International Bureau of WIPO, Geneva, Switzerland.

(Continued)

*Primary Examiner* — Gary B Nickol
*Assistant Examiner* — Khatol S Shahnan Shah
(74) *Attorney, Agent, or Firm* — Sterne, Kessler, Goldstein & Fox P.L.L.C.

(57) ABSTRACT

The present invention discloses a *Salmonella paratyphi* A with an O-antigen having an extended carbohydrate chain and uses thereof. The method comprises the following steps: inactivating an cld gene encoding an enzyme controlling chain length of O-antigen of a *Salmonella paratyphi* A strain to obtain a *Salmonella paratyphi* A with deletion of cld gene; allowing overexpression of $cld_{LT2}$ gene encoding an enzyme controlling chain length of O-antigen of *Salmonella typhimurium* in *Salmonella paratyphi* A deficient in the cld gene encoding an enzyme controlling chain length of O-antigen, so as to extend carbohydrate chain length of O-antigen. Both of the *Salmonella paratyphi* A O-polysaccharide-recombinant fusion protein conjugate vaccines $rCTB4573_3$-$OPS_{Spty50973}$ and rEPA4573-$OPS_{Spty50973}$ as prepared by using *Salmonella paratyphi* A with an O-antigen having an extended carbohydrate chain can induce mice to generate specific antibodies against *Salmonella paratyphi* A, and their antibody titers are significantly improved.

3 Claims, 4 Drawing Sheets

Specification includes a Sequence Listing.

(56) References Cited

OTHER PUBLICATIONS

Cohen, Jo et al., "Identification of *Salmonella* O antigens by coagglutination," Progress in Microbiology and Immunology, No. 01, Feb. 28, 1985, p. 59, Issn 1005-5673: China Academic Journals Full-text Database, CNKI p. 61, China.
Cohen, Jo et al., "Identification of *Salmonella* O antigens by coagglutination," J. Clin. Microbiol. 19(5): 576-578 (May 1984), American Society for Microbiology, Washington, DC.
Extended European search report including the supplementary European search report and the European search opinion, for EP Appl. No. 15867235.2, dated Apr. 25, 2018, European Patent Office, Munich, Germany.
Micoli, F. et al., "A scalable method for O-antigen purification applied to various *Salmonella* serovars," Anal Biochem. Mar. 1, 2013;434(1):136-45. doi: 10.1016/j.ab.2012.10.038. Epub Nov. 7, 2012, Elsevier, San Diego, CA.
Ihssen, J. et al., "Production of glycoprotein vaccines in *Escherichia coli*," Microb Cell Fact. Aug. 11, 2010;9:61. doi: 10.1186/1475-2859-9-61, 13 pages, BioMed Central, London, England.
Faridmoayer, A. et al., "Extreme substrate promiscuity of the *Neisseria* oligosaccharyl transferase involved in protein O-glycosylation, " J Biol Chem. Dec. 12, 2008;283(50):34596-604. doi: 10.1074/jbc.M807113200. Epub Oct. 17, 2008, Am. Soc. Biochem. Mol. Biol., Baltimore, MD.
Murray, G.L. et al. "Altering the length of the lipopolysaccharide O antigen has an impact on the interaction of *Salmonella enterica* serovar Typhimurium with macrophages and complement," J Bacteriol. Apr. 2006;188(7):2735-9, Am. Soc. Microbiol., Washington, DC.
Datsenko, K.A. et al., "One-step inactivation of chromosomal genes in *Escherichia coli* K-12 using PCR products," Proc Natl Acad Sci U S A. Jun. 6, 2000;97(12):6640-5, National Academy of Sciences, Washington, DC.
Chaveroche, M.-K. et al., "A rapid method for efficient gene replacement in the filamentous fungus *Aspergillus nidulans*," Nucleic Acids Res. Nov. 15, 2000;28(22):e97, 6 pages, Oxford University Press, Oxford, England.
Pan, C. et al., "Biosynthesis of Conjugate Vaccines Using an O-Linked Glycosylation System," mBio 7:2 Mar./Apr. 2016; doi:10.1128/mBio.00443-16, 11 pages, Am. Soc. Microbiol., Washington, DC.
Sun, P. et al., "Design and production of conjugate vaccines against S. Paratyphi A using an O-linked glycosylation system in vivo," NPJ Vaccines. Feb. 5, 2018;3:4. doi: 10.1038/s41541-017-0037-1. eCollection 2018, 9 pages, Springer Nature in partnership with the Sealy Center for Vaccine Development, London, England.
Database UniProt [Online] Accession No. UNIPROT:A0A0D6FGW8, May 27, 2015, sequence version 1, entry version 29, SubName: Full=Chain length determinant protein {ECO:0000313 | EMBO:PHK79504.1}; (PJL89668.1); SubName: Full=Chain length determinant protein WzzB, {ECO:0000313 |0 EMBL:KTZ12448.1}.
First Office Action for CN Appl. No. 201410743690.X, dated Oct. 29, 2018, from the State Intellectual Property Office of People's Republic of China, Beijing, CN.
Peng, Z. et al., "Preparation and immunogenicity-evaluation of typhoid O-specific polysaccharides bio-conjugate vaccines," Yi Chuan. (Hereditas) May 2015;37(5):473-9. doi: 10.16288/j.yczz.15-001, Beijing, China.
Jiang, N, "A novel construct of attenuated *Salmonella* vaccine vector," A Thesis for Master's Degree, Academy of Military Medical Sciences P.L.A. China, May 21, 2009.
Genbank Accession No. AEF07997.1, Lipopolysaccharide O-antigen chain length regulator [*Salmonella enterica* subsp. Enterica serovar Typhimurium str. UK-1], Jan. 30, 2014 version AEF07997.1.
Dai, Q-L et al., "Research advances in O-antigen polysaccharide of *Salmonella enterica*, "Microbiology China 43(8):1829-1835 (Aug. 20, 2016).
Liu, D et al, "Transferases of O-antigen biosynthesis in *Salmonella enterica*: dideoxyhexosyltransferases of groups B and C2 and acetyltransferase of group C2," J Bacteriol. Jul. 1995;177(14):4084-8.
Verma, NK et al., O-antigen variation in *Salmonella* spp.: *rfb* gene clusters of three strains, J Bacteriol. Jan. 1988;170(1):103-7.
Sun, P. et al. "Design and production of conjugate vaccines against S. Paratyphi A using an O-linked gycosylation system in vivo," npj Vaccines Feb. 4, 2018:1-9, supplemental material. doi:10.1038/s41541-017-0037-1.
Sun, Hualu: "Insolation and Identification of Salmonella, Construction and Biological Characteristics of Deletion Mutants of Genes for Biofilm Formation from Salmonella Pullorum," May, 2012; Agriculture, China Master's Theses Full-Text Database, No. 7, Jul. 15, 2013 (2013-07-15), 63 pp., CNKI p. D050-191, China.
Examination Report for IN Appl. No. 201717023513, dated Jun. 16, 2020, for the Intellectual Property India, New Delhi, India.

* cited by examiner rEPA4573-$OPS_{Spty50973}$ rCTB4573$_3$-$OPS_{Spty50973}$

SEQUENCE LISTING

```
<160> NUMBER OF SEQ ID NOS: 34

<210> SEQ ID NO 1
<211> LENGTH: 987
<212> TYPE: DNA
<213> ORGANISM: Artificial Sequence
<220> FEATURE:
<223> OTHER INFORMATION: enzyme (Cld)LT2 controlling chain length of O-
      antigen of Salmonella typhimurium

<400> SEQUENCE: 1

atgacagtgg acagtaatac cagcagtggc cgtggtaacg atcctgagca gatcgacctg     60

attgagctgc tgctgcaact gtggcgtggc aagatgacca tcatcgtggc cgtgatcatc    120

gccattctgc tggccgtggg ctatctgatg atcgccaagg aaaagtggac cagcaccgcc    180

atcatcaccc agccggatgc cgcacaagtg gcaacctaca caaacgccct gaatgtgctg    240

tacggcggta acgcaccgaa gattagtgag gtgcaggcca acttcatcag ccgtttcagc    300

agcgcattca gcgccttaag cgaggtgctg gataaccaga aggagcgtga aaagctgacc    360

atcgagcaga gcgtgaaagg tcaagccctg cctctgagcg ttagctatgt gagtaccacc    420
```

-continued

```
gcagaaggtg cccaacgtcg tctggccgag tacatccaac aggtggatga agaggtggcc    480

aaggaactgg aggtggatct gaaggacaac atcaccctgc agaccaagac cctgcaggag    540

agcctggaaa cccaggaagt ggtggcccag gaacagaaag acctgcgcat caagcagatc    600

gaagaggccc tgcgttacgc cgatgaagca aagatcaccc aaccgcagat ccaacagaca    660

caagacgtga cccaggacac aatgttcctg ctgggtagcg acgccctgaa aagcatgatc    720

cagaacgagg ccacacgtcc gctggtgttt agcccggcct actaccagac caaacagacc    780

ctgctggata ttaagaacct gaaagtgacc gccgacaccg tgcacgtgta ccgctacgtg    840

atgaaaccta ccctgccggt tcgtcgtgac agtcctaaga ccgcaatcac actggttctg    900

gcagtgctgt taggcggtat gattggcgca ggcatcgtgt taggccgtaa cgccttacgc    960

agctacaagc ctaaagcctt ataatga                                        987
```

```
<210> SEQ ID NO 2
<211> LENGTH: 327
<212> TYPE: PRT
<213> ORGANISM: Artificial Sequence
<220> FEATURE:
<223> OTHER INFORMATION: enzyme (Cld)LT2 controlling chain length of O-
      antigen of Salmonella typhimurium

<400> SEQUENCE: 2

Met Thr Val Asp Ser Asn Thr Ser Ser Gly Arg Gly Asn Asp Pro Glu
1               5                   10                  15

Gln Ile Asp Leu Ile Glu Leu Leu Leu Gln Leu Trp Arg Gly Lys Met
            20                  25                  30

Thr Ile Ile Val Ala Val Ile Ile Ala Ile Leu Leu Ala Val Gly Tyr
        35                  40                  45

Leu Met Ile Ala Lys Glu Lys Trp Thr Ser Thr Ala Ile Ile Thr Gln
    50                  55                  60

Pro Asp Ala Ala Gln Val Ala Thr Tyr Thr Asn Ala Leu Asn Val Leu
65                  70                  75                  80

Tyr Gly Gly Asn Ala Pro Lys Ile Ser Glu Val Gln Ala Asn Phe Ile
                85                  90                  95

Ser Arg Phe Ser Ser Ala Phe Ser Ala Leu Ser Glu Val Leu Asp Asn
            100                 105                 110

Gln Lys Glu Arg Glu Lys Leu Thr Ile Glu Gln Ser Val Lys Gly Gln
        115                 120                 125

Ala Leu Pro Leu Ser Val Ser Tyr Val Ser Thr Thr Ala Glu Gly Ala
    130                 135                 140

Gln Arg Arg Leu Ala Glu Tyr Ile Gln Gln Val Asp Glu Glu Val Ala
145                 150                 155                 160

Lys Glu Leu Glu Val Asp Leu Lys Asp Asn Ile Thr Leu Gln Thr Lys
                165                 170                 175

Thr Leu Gln Glu Ser Leu Glu Thr Gln Glu Val Val Ala Gln Glu Gln
            180                 185                 190

Lys Asp Leu Arg Ile Lys Gln Ile Glu Glu Ala Leu Arg Tyr Ala Asp
        195                 200                 205

Glu Ala Lys Ile Thr Gln Pro Gln Ile Gln Gln Thr Gln Asp Val Thr
    210                 215                 220

Gln Asp Thr Met Phe Leu Leu Gly Ser Asp Ala Leu Lys Ser Met Ile
225                 230                 235                 240

Gln Asn Glu Ala Thr Arg Pro Leu Val Phe Ser Pro Ala Tyr Tyr Gln
                245                 250                 255
```

-continued

Thr Lys Gln Thr Leu Leu Asp Ile Lys Asn Leu Lys Val Thr Ala Asp
260 265 270

Thr Val His Val Tyr Arg Tyr Val Met Lys Pro Thr Leu Pro Val Arg
275 280 285

Arg Asp Ser Pro Lys Thr Ala Ile Thr Leu Val Leu Ala Val Leu Leu
290 295 300

Gly Gly Met Ile Gly Ala Gly Ile Val Leu Gly Arg Asn Ala Leu Arg
305 310 315 320

Ser Tyr Lys Pro Lys Ala Leu
325

<210> SEQ ID NO 3
<211> LENGTH: 2025
<212> TYPE: DNA
<213> ORGANISM: Artificial Sequence
<220> FEATURE:
<223> OTHER INFORMATION: fusion protein rEPA4573 of recombinant
Pseudomonas aeruginosa exotoxin A

<400> SEQUENCE: 3
atgaaaaaga tttggctggc gctggctggt ttagttttag cgtttagcgc atcggcggcc 60
gaggaagcct tcgacctctg gaacgaatgc gccaaagcct gcgtgctcga cctcaaggac 120
ggcgtgcgtt ccagccgcat gagcgtcgac ccggccatcg ccgacaccaa cggccagggc 180
gtgctgcact actccatggt cctggagggc ggcaacgacg cgctcaagct ggccatcgac 240
aacgccctca gcatcaccag cgacggcctg accatccgcc tcgaaggcgg cgtcgagccg 300
aacaagccgg tgcgctacag ctacacgcgc caggcgcgcg gcagttggtc gctgaactgg 360
ctggtaccga tcggccacga gaagccctcg aacatcaagg tgttcatcca cgaactgaac 420
gccggtaacc agctcagcca catgtcgccg atctacacca tcgagatggg cgacgagttg 480
ctggcgaagc tggcgcgcga tgccaccttc ttcgtcaggg cgcacgagag caacgagatg 540
cagccgacgc tcgccatcag ccatgccggg gtcagcgtgg tcatggccca ggcccagccg 600
cgccgggaaa agcgctggag cgaatgggcc agcggcaagg tgttgtgcct gctcgacccg 660
ctggacgggg tctacaacta cctcgcccag cagcgctgca acctcgacga tacctgggaa 720
ggcaagatct accgggtgct cgccggcaac ccggcgaagc atgacctgga catcaagccc 780
acggtcatca gtcatcgcct gcacttcccc gagggcggca gcctggccgc gctgaccgcg 840
caccaggctt gccacctgcc gctggagact ttcacccgtc atcgccagcc gcgcggctgg 900
gaacaactgg agcagtgcgg ctatccggtg cagcggctgg tcgccctcta cctggcggcg 960
cggctgtcgt ggaaccaggt cgaccaggtg atcggcaacg ccctggccag ccccggcagc 1020
ggcggcgacc tgggcgaagc gatccgcgag cagccggagc aggcccgtct ggccctgacc 1080
ctggccgccg ccgagagcga gcgcttcgtc cggcagggca ccggcaacga cgaggccggc 1140
gcggccagcg ccgacgtggt gagcctgacc tgcccggtcg ccgccggtga atgcgcgggc 1200
ccggcggaca gcggcgacgc cctgctggag cgcaactatc ccactggcgc ggagttcctc 1260
ggcgacggcg gcgacatcag cttcagcacc cgcggcacgc agaactggac ggtggagcgg 1320
ctgctccagg cgcaccgcca actggaggag cgcggctatg tgttcgtcgg ctaccacggc 1380
accttcctcg aagcggcgca aagcatcgtc ttcggcgggg tgcgcgcgcg cagccaggac 1440
ctcgacgcga tctggcgcgg tttctatatc gccggcgatc cggcgctggc ctacggctac 1500
gcccaggacc aggaacccga cgcgcgcggc cggatccgca acggtgccct gctgcgggtc 1560
tatgtgccgc gctcgagcct gccgggcttc taccgcaccg gcctgaccct ggccgcgccg 1620

-continued

```
gaggcggcgg gcgaggtcga acggctgatc ggccatccgc tgccgctgcg cctggacgcc   1680

atcaccggcc ccgaggagga aggcgggcgc gtgaccattc tcggctggcc gctggccgag   1740

cgcaccgtgg tgattccctc ggcgatcccc accgacccgc gcaacgtcgg cggcgacctc   1800

gacccgtcca gcatccccga caaggaacag gcgatcagcg ccctgccgga ctacgccagc   1860

cagcccggca aaccgccgcg cgaggacctg aaggatcaga acgcgacctc agccgttacc   1920

gagtattacc tgaatcacgg cgaatggccc ggcaacaaca cttctgccgg cgtggcaacc   1980

tcctctgaaa tcaaaggagg tggacaccac caccaccacc actaa                   2025


<210> SEQ ID NO 4
<211> LENGTH: 674
<212> TYPE: PRT
<213> ORGANISM: Artificial Sequence
<220> FEATURE:
<223> OTHER INFORMATION: fusion protein rEPA4573 of recombinant
      Pseudomonas aeruginosa exotoxin A

<400> SEQUENCE: 4

Met Lys Lys Ile Trp Leu Ala Leu Ala Gly Leu Val Leu Ala Phe Ser
1               5                   10                  15

Ala Ser Ala Ala Glu Glu Ala Phe Asp Leu Trp Asn Glu Cys Ala Lys
            20                  25                  30

Ala Cys Val Leu Asp Leu Lys Asp Gly Val Arg Ser Ser Arg Met Ser
        35                  40                  45

Val Asp Pro Ala Ile Ala Asp Thr Asn Gly Gln Gly Val Leu His Tyr
    50                  55                  60

Ser Met Val Leu Glu Gly Gly Asn Asp Ala Leu Lys Leu Ala Ile Asp
65                  70                  75                  80

Asn Ala Leu Ser Ile Thr Ser Asp Gly Leu Thr Ile Arg Leu Glu Gly
                85                  90                  95

Gly Val Glu Pro Asn Lys Pro Val Arg Tyr Ser Tyr Thr Arg Gln Ala
            100                 105                 110

Arg Gly Ser Trp Ser Leu Asn Trp Leu Val Pro Ile Gly His Glu Lys
        115                 120                 125

Pro Ser Asn Ile Lys Val Phe Ile His Glu Leu Asn Ala Gly Asn Gln
    130                 135                 140

Leu Ser His Met Ser Pro Ile Tyr Thr Ile Glu Met Gly Asp Glu Leu
145                 150                 155                 160

Leu Ala Lys Leu Ala Arg Asp Ala Thr Phe Phe Val Arg Ala His Glu
                165                 170                 175

Ser Asn Glu Met Gln Pro Thr Leu Ala Ile Ser His Ala Gly Val Ser
            180                 185                 190

Val Val Met Ala Gln Ala Gln Pro Arg Arg Glu Lys Arg Trp Ser Glu
        195                 200                 205

Trp Ala Ser Gly Lys Val Leu Cys Leu Leu Asp Pro Leu Asp Gly Val
    210                 215                 220

Tyr Asn Tyr Leu Ala Gln Gln Arg Cys Asn Leu Asp Asp Thr Trp Glu
225                 230                 235                 240

Gly Lys Ile Tyr Arg Val Leu Ala Gly Asn Pro Ala Lys His Asp Leu
                245                 250                 255

Asp Ile Lys Pro Thr Val Ile Ser His Arg Leu His Phe Pro Glu Gly
            260                 265                 270

Gly Ser Leu Ala Ala Leu Thr Ala His Gln Ala Cys His Leu Pro Leu
        275                 280                 285
```

```
Glu Thr Phe Thr Arg His Arg Gln Pro Arg Gly Trp Glu Gln Leu Glu
    290                 295                 300

Gln Cys Gly Tyr Pro Val Gln Arg Leu Val Ala Leu Tyr Leu Ala Ala
305                 310                 315                 320

Arg Leu Ser Trp Asn Gln Val Asp Gln Val Ile Gly Asn Ala Leu Ala
                325                 330                 335

Ser Pro Gly Ser Gly Gly Asp Leu Gly Glu Ala Ile Arg Glu Gln Pro
            340                 345                 350

Glu Gln Ala Arg Leu Ala Leu Thr Leu Ala Ala Ala Glu Ser Glu Arg
        355                 360                 365

Phe Val Arg Gln Gly Thr Gly Asn Asp Glu Ala Gly Ala Ala Ser Ala
    370                 375                 380

Asp Val Val Ser Leu Thr Cys Pro Val Ala Ala Gly Glu Cys Ala Gly
385                 390                 395                 400

Pro Ala Asp Ser Gly Asp Ala Leu Leu Glu Arg Asn Tyr Pro Thr Gly
                405                 410                 415

Ala Glu Phe Leu Gly Asp Gly Gly Asp Ile Ser Phe Ser Thr Arg Gly
            420                 425                 430

Thr Gln Asn Trp Thr Val Glu Arg Leu Leu Gln Ala His Arg Gln Leu
        435                 440                 445

Glu Glu Arg Gly Tyr Val Phe Val Gly Tyr His Gly Thr Phe Leu Glu
    450                 455                 460

Ala Ala Gln Ser Ile Val Phe Gly Gly Val Arg Ala Arg Ser Gln Asp
465                 470                 475                 480

Leu Asp Ala Ile Trp Arg Gly Phe Tyr Ile Ala Gly Asp Pro Ala Leu
                485                 490                 495

Ala Tyr Gly Tyr Ala Gln Asp Gln Glu Pro Asp Ala Arg Gly Arg Ile
            500                 505                 510

Arg Asn Gly Ala Leu Leu Arg Val Tyr Val Pro Arg Ser Ser Leu Pro
        515                 520                 525

Gly Phe Tyr Arg Thr Gly Leu Thr Leu Ala Ala Pro Glu Ala Ala Gly
    530                 535                 540

Glu Val Glu Arg Leu Ile Gly His Pro Leu Pro Leu Arg Leu Asp Ala
545                 550                 555                 560

Ile Thr Gly Pro Glu Glu Glu Gly Gly Arg Val Thr Ile Leu Gly Trp
                565                 570                 575

Pro Leu Ala Glu Arg Thr Val Val Ile Pro Ser Ala Ile Pro Thr Asp
            580                 585                 590

Pro Arg Asn Val Gly Gly Asp Leu Asp Pro Ser Ser Ile Pro Asp Lys
        595                 600                 605

Glu Gln Ala Ile Ser Ala Leu Pro Asp Tyr Ala Ser Gln Pro Gly Lys
    610                 615                 620

Pro Pro Arg Glu Asp Leu Lys Asp Gln Asn Ala Thr Ser Ala Val Thr
625                 630                 635                 640

Glu Tyr Tyr Leu Asn His Gly Glu Trp Pro Gly Asn Asn Thr Ser Ala
                645                 650                 655

Gly Val Ala Thr Ser Ser Glu Ile Lys Gly Gly Gly His His His His
            660                 665                 670

His His
```

<210> SEQ ID NO 5
<211> LENGTH: 501
<212> TYPE: DNA

<213> ORGANISM: Artificial Sequence
<220> FEATURE:
<223> OTHER INFORMATION: fusion protein rCTB4573 of recombinant cholera toxin B subunit

<400> SEQUENCE: 5

```
atgaagaaaa tttggctggc cttagccggc ctggttctgg cattcagcgc cagcgcaacc     60

ccgcagaaca tcaccgacct gtgcgccgag taccacaaca cccaaattta taccctgaac    120

gacaaaattt ttagctacac cgagagcctg gcaggcaagc gcgagatggc catcatcacc    180

ttcaagaacg gcgccatttt ccaggtggag gtgccgggca gccagcacat cgacagtcag    240

aagaaggcca tcgagcgcat gaaggacacc ctgcgcatcg cctacctgac cgaggccaag    300

gtggagaagc tgtgcgtgtg gaacaacaag accccgcacg ccatcgccgc aatcagcatg    360

gccaacgacc agaacgccac cagcgccgtg accgagtact atctgaacca tggcgagtgg    420

ccgggtaata acaccagcgc cggcgtggcc acaagcagtg agatcaaggg cggcggatcc    480

caccatcacc accaccatta a                                              501
```

<210> SEQ ID NO 6
<211> LENGTH: 166
<212> TYPE: PRT
<213> ORGANISM: Artificial Sequence
<220> FEATURE:
<223> OTHER INFORMATION: fusion protein rCTB4573 of recombinant cholera toxin B subunit

<400> SEQUENCE: 6

```
Met Lys Lys Ile Trp Leu Ala Leu Ala Gly Leu Val Leu Ala Phe Ser
1               5                   10                  15

Ala Ser Ala Thr Pro Gln Asn Ile Thr Asp Leu Cys Ala Glu Tyr His
            20                  25                  30

Asn Thr Gln Ile Tyr Thr Leu Asn Asp Lys Ile Phe Ser Tyr Thr Glu
        35                  40                  45

Ser Leu Ala Gly Lys Arg Glu Met Ala Ile Ile Thr Phe Lys Asn Gly
    50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
    130                 135                 140

Thr Ser Ala Gly Val Ala Thr Ser Ser Glu Ile Lys Gly Gly Gly Ser
145                 150                 155                 160

His His His His His His
                165
```

<210> SEQ ID NO 7
<211> LENGTH: 1815
<212> TYPE: DNA
<213> ORGANISM: Artificial Sequence
<220> FEATURE:
<223> OTHER INFORMATION: Neisseria meningitides oligosaccharyltransferase pglL

<400> SEQUENCE: 7

-continued

```
atgcccgctg aaacgaccgt atccggcgcg caccccgccg ccaaactgcc gatttacatc     60

ctgccctgct tcctttggat aggcatcgtc ccctttacct tcgcgctcaa actgaaaccg    120

tcgcccgact tttaccacga tgccgccgcc gcagccggcc tgattgtcct gttgttcctc    180

acggcaggaa aaaaactgtt tgatgtcaaa atccccgcca tcagcttcct tctgtttgca    240

atggcggcgt tttggtatct tcaggcacgc ctgatgaacc tgatttaccc cggtatgaac    300

gacatcgtct cttggatttt catcttgctc gccgtcagcg cgtgggcctg ccggagcttg    360

gtcgcacact tcggacaaga acgcatcgtg accctgtttg cctggtcgct gcttatcggc    420

tccctgcttc aatcctgcat cgtcgtcatc cagtttgccg gctgggaaga cacccctctg    480

tttcaaaaca tcatcgttta cagcgggcaa ggcgtaatcg gacacatcgg gcagcgcaac    540

aacctcggac actacctcat gtggggcata ctcgccgccg cctacctcaa cggacaacga    600

aaaatccccg ccgccctcgg cgtaatctgc ctgattatgc agaccgccgt tttaggtttg    660

gtcaactcgc gcaccatctt gacctacata gccgccatcg ccctcatcct tcccttctgg    720

tatttccgtt cggacaaatc caacaggcgg acgatgctcg gcatagccgc agccgtattc    780

cttaccgcgc tgttccaatt ttccatgaac accattctgg aaacctttac tggcatccgc    840

tacgaaactg ccgtcgaacg cgtcgccaac ggcggtttca cagacttgcc gcgccaaatc    900

gaatggaata aagcccttgc cgccttccag tccgccccga tattcgggca cggctggaac    960

agttttgccc aacaaacctt cctcatcaat gccgaacagc acaacatata cgacaacctc   1020

ctcagcaact tgttcaccca ttcccacaac atcgtcctcc aactccttgc agagatggga   1080

atcagcggca cgcttctggt tgccgcaacc ctgctgacgg gcattgccgg gctgcttaaa   1140

cgccccctga cccccgcatc gcttttccta atctgcacgc ttgccgtcag tatgtgccac   1200

agtatgctcg aatatccttt gtggtatgtc tatttcctca tccctttcgg actgatgctc   1260

ttcctgtccc ccgcagaggc ttcagacggc atcgccttca aaaaagccgc caatctcggc   1320

atactgaccg cctccgccgc catattcgca ggattgctgc acttggactg gacatacacc   1380

cggctggtta acgccttttc ccccgccact gacgacagtg ccaaaaccct caaccggaaa   1440

atcaacgagt tgcgctatat ttccgcaaac agtccgatgc tgtcctttta tgccgacttc   1500

tccctcgtaa acttcgccct gccggaatac cccgaaaccc agacttgggc ggaagaagca   1560

accctcaaat cactaaaata ccgcccccac tccgccacct accgcatcgc cctctacctg   1620

atgcggcaag gcaaagttgc agaagcaaaa caatggatgc gggcgacaca gtcctattac   1680

ccctacctga tgccccgata cgccgacgaa atccgcaaac tgcccgtatg ggcgccgctg   1740

ctacccgaac tgctcaaaga ctgcaaagcc ttcgccgccg cgcccggtca tccggaagca   1800

aaaccctgca aatga                                                    1815
```

<210> SEQ ID NO 8
<211> LENGTH: 604
<212> TYPE: PRT
<213> ORGANISM: Artificial Sequence
<220> FEATURE:
<223> OTHER INFORMATION: Neisseria meningitidis O-oligosaccharide transferase PglL

<400> SEQUENCE: 8

```
Met Pro Ala Glu Thr Thr Val Ser Gly Ala His Pro Ala Ala Lys Leu
1               5                   10                  15

Pro Ile Tyr Ile Leu Pro Cys Phe Leu Trp Ile Gly Ile Val Pro Phe
            20                  25                  30
```

-continued

```
Thr Phe Ala Leu Lys Leu Lys Pro Ser Pro Asp Phe Tyr His Asp Ala
        35                  40                  45

Ala Ala Ala Ala Gly Leu Ile Val Leu Leu Phe Leu Thr Ala Gly Lys
    50                  55                  60

Lys Leu Phe Asp Val Lys Ile Pro Ala Ile Ser Phe Leu Leu Phe Ala
65                  70                  75                  80

Met Ala Ala Phe Trp Tyr Leu Gln Ala Arg Leu Met Asn Leu Ile Tyr
                85                  90                  95

Pro Gly Met Asn Asp Ile Val Ser Trp Ile Phe Ile Leu Leu Ala Val
            100                 105                 110

Ser Ala Trp Ala Cys Arg Ser Leu Val Ala His Phe Gly Gln Glu Arg
        115                 120                 125

Ile Val Thr Leu Phe Ala Trp Ser Leu Leu Ile Gly Ser Leu Leu Gln
    130                 135                 140

Ser Cys Ile Val Val Ile Gln Phe Ala Gly Trp Glu Asp Thr Pro Leu
145                 150                 155                 160

Phe Gln Asn Ile Ile Val Tyr Ser Gly Gln Gly Val Ile Gly His Ile
                165                 170                 175

Gly Gln Arg Asn Asn Leu Gly His Tyr Leu Met Trp Gly Ile Leu Ala
            180                 185                 190

Ala Ala Tyr Leu Asn Gly Gln Arg Lys Ile Pro Ala Ala Leu Gly Val
        195                 200                 205

Ile Cys Leu Ile Met Gln Thr Ala Val Leu Gly Leu Val Asn Ser Arg
    210                 215                 220

Thr Ile Leu Thr Tyr Ile Ala Ala Ile Ala Leu Ile Leu Pro Phe Trp
225                 230                 235                 240

Tyr Phe Arg Ser Asp Lys Ser Asn Arg Arg Thr Met Leu Gly Ile Ala
                245                 250                 255

Ala Ala Val Phe Leu Thr Ala Leu Phe Gln Phe Ser Met Asn Thr Ile
            260                 265                 270

Leu Glu Thr Phe Thr Gly Ile Arg Tyr Glu Thr Ala Val Glu Arg Val
        275                 280                 285

Ala Asn Gly Gly Phe Thr Asp Leu Pro Arg Gln Ile Glu Trp Asn Lys
    290                 295                 300

Ala Leu Ala Ala Phe Gln Ser Ala Pro Ile Phe Gly His Gly Trp Asn
305                 310                 315                 320

Ser Phe Ala Gln Gln Thr Phe Leu Ile Asn Ala Glu Gln His Asn Ile
                325                 330                 335

Tyr Asp Asn Leu Leu Ser Asn Leu Phe Thr His Ser His Asn Ile Val
            340                 345                 350

Leu Gln Leu Leu Ala Glu Met Gly Ile Ser Gly Thr Leu Leu Val Ala
        355                 360                 365

Ala Thr Leu Leu Thr Gly Ile Ala Gly Leu Leu Lys Arg Pro Leu Thr
    370                 375                 380

Pro Ala Ser Leu Phe Leu Ile Cys Thr Leu Ala Val Ser Met Cys His
385                 390                 395                 400

Ser Met Leu Glu Tyr Pro Leu Trp Tyr Val Tyr Phe Leu Ile Pro Phe
                405                 410                 415

Gly Leu Met Leu Phe Leu Ser Pro Ala Glu Ala Ser Asp Gly Ile Ala
            420                 425                 430

Phe Lys Lys Ala Ala Asn Leu Gly Ile Leu Thr Ala Ser Ala Ala Ile
        435                 440                 445
```

-continued

```
Phe Ala Gly Leu Leu His Leu Asp Trp Thr Tyr Thr Arg Leu Val Asn
    450                 455                 460

Ala Phe Ser Pro Ala Thr Asp Asp Ser Ala Lys Thr Leu Asn Arg Lys
465                 470                 475                 480

Ile Asn Glu Leu Arg Tyr Ile Ser Ala Asn Ser Pro Met Leu Ser Phe
                485                 490                 495

Tyr Ala Asp Phe Ser Leu Val Asn Phe Ala Leu Pro Glu Tyr Pro Glu
            500                 505                 510

Thr Gln Thr Trp Ala Glu Glu Ala Thr Leu Lys Ser Leu Lys Tyr Arg
        515                 520                 525

Pro His Ser Ala Thr Tyr Arg Ile Ala Leu Tyr Leu Met Arg Gln Gly
    530                 535                 540

Lys Val Ala Glu Ala Lys Gln Trp Met Arg Ala Thr Gln Ser Tyr Tyr
545                 550                 555                 560

Pro Tyr Leu Met Pro Arg Tyr Ala Asp Glu Ile Arg Lys Leu Pro Val
                565                 570                 575

Trp Ala Pro Leu Leu Pro Glu Leu Leu Lys Asp Cys Lys Ala Phe Ala
            580                 585                 590

Ala Ala Pro Gly His Pro Glu Ala Lys Pro Cys Lys
        595                 600


<210> SEQ ID NO 9
<211> LENGTH: 699
<212> TYPE: DNA
<213> ORGANISM: Artificial Sequence
<220> FEATURE:
<223> OTHER INFORMATION: fusion protein (rCTB4573)3 of recombinant
      cholera toxin B subunit

<400> SEQUENCE: 9

atgaagaaaa tttggctggc cttagccggc ctggttctgg cattcagcgc cagcgcaacc      60

ccgcagaaca tcaccgacct gtgcgccgag taccacaaca cccaaattta taccctgaac     120

gacaaaattt ttagctacac cgagagcctg gcaggcaagc gcgagatggc catcatcacc     180

ttcaagaacg gcgccatttt ccaggtggag gtgccgggca gccagcacat cgacagtcag     240

aagaaggcca tcgagcgcat gaaggacacc ctgcgcatcg cctacctgac cgaggccaag     300

gtggagaagc tgtgcgtgtg gaacaacaag accccgcacg ccatcgccgc aatcagcatg     360

gccaacgacc agaacgccac cagcgccgtg accgagtact atctgaacca tggcgagtgg     420

ccgggtaata acaccagcgc cggcgtggcc acaagcagtg agatcaaggg cggcggatct     480

agcgccgtga ccgagtacta tctgaaccat ggcgagtggc cgggtaataa caccagcgcc     540

ggcgtggcca caagcagtga gatcaagggc ggcggatcta gcgccgtgac cgagtactat     600

ctgaaccatg gcgagtggcc gggtaataac accagcgccg gcgtggccac aagcagtgag     660

atcaagggcg gcggatccca ccatcaccac caccattaa                             699


<210> SEQ ID NO 10
<211> LENGTH: 232
<212> TYPE: PRT
<213> ORGANISM: Artificial Sequence
<220> FEATURE:
<223> OTHER INFORMATION: fusion protein (rCTB4573)3 of recombinant
      cholera toxin B subunit

<400> SEQUENCE: 10

Met Lys Lys Ile Trp Leu Ala Leu Ala Gly Leu Val Leu Ala Phe Ser
1               5                   10                  15
```

-continued

```
Ala Ser Ala Thr Pro Gln Asn Ile Thr Asp Leu Cys Ala Glu Tyr His
            20                  25                  30

Asn Thr Gln Ile Tyr Thr Leu Asn Asp Lys Ile Phe Ser Tyr Thr Glu
        35                  40                  45

Ser Leu Ala Gly Lys Arg Glu Met Ala Ile Ile Thr Phe Lys Asn Gly
    50                  55                  60

Ala Ile Phe Gln Val Glu Val Pro Gly Ser Gln His Ile Asp Ser Gln
65                  70                  75                  80

Lys Lys Ala Ile Glu Arg Met Lys Asp Thr Leu Arg Ile Ala Tyr Leu
                85                  90                  95

Thr Glu Ala Lys Val Glu Lys Leu Cys Val Trp Asn Asn Lys Thr Pro
            100                 105                 110

His Ala Ile Ala Ala Ile Ser Met Ala Asn Asp Gln Asn Ala Thr Ser
        115                 120                 125

Ala Val Thr Glu Tyr Tyr Leu Asn His Gly Glu Trp Pro Gly Asn Asn
    130                 135                 140

Thr Ser Ala Gly Val Ala Thr Ser Ser Glu Ile Lys Gly Gly Gly Ser
145                 150                 155                 160

Ser Ala Val Thr Glu Tyr Tyr Leu Asn His Gly Glu Trp Pro Gly Asn
                165                 170                 175

Asn Thr Ser Ala Gly Val Ala Thr Ser Ser Glu Ile Lys Gly Gly Gly
            180                 185                 190

Ser Ser Ala Val Thr Glu Tyr Tyr Leu Asn His Gly Glu Trp Pro Gly
        195                 200                 205

Asn Asn Thr Ser Ala Gly Val Ala Thr Ser Ser Glu Ile Lys Gly Gly
    210                 215                 220

Gly Ser His His His His His His
225                 230
```

<210> SEQ ID NO 11
<211> LENGTH: 2102
<212> TYPE: DNA
<213> ORGANISM: Artificial Sequence
<220> FEATURE:
<223> OTHER INFORMATION: linear targeting DNA fragment 1 containing a cat gene

<400> SEQUENCE: 11

```
cagttgctgg ctaattatca gtcagtgcct aataatatta tctccgctat cgttgaagca      60

aaccgtacgc gtaaagattt tattgccgat tctatccttg ccagaaagcc taaagtggtg     120

ggcatttatc gcctgattat gaagagtggc tccgataact tccgcgcctc atcgattcag     180

gggattatga aacgtattaa agcgaaaggc gtagaggtca tcatctatga gccggtaatg     240

caagaagaaa ctttctttaa ctcacgtctt gaacgtgatt tgcactgctt taaacagcag     300

gcggatgtca ttatttccaa tcggatggcg gcagagcttt tggatgtcgc tgaaaaagtg     360

tatacccgcg atcttttcgg tagtgattaa taaggcaatc ggggctgatg agtcccaatg     420

atttattgac caaatggaaa taatgtctga tttttatcat taatcctatg gcatatattt     480

tctttatgac tacactgtct ccagcttcat cctttttta gttagggtat ctatgacaag     540

cgattgtgta ggctggagct gcttcgaagt tcctatactt tctagagaat aggaacttcg     600

gaataggaac ttcatttaaa tggcgcgcct tacgccccgc cctgccactc atcgcagtac     660

tgttgtattc attaagcatc tgccgacatg gaagccatca caaacggcat gatgaacctg     720

aatcgccagc ggcatcagca ccttgtcgcc ttgcgtataa tatttgccca tggtgaaaac     780
```

-continued gggggcgaag aagttgtcca tattggccac gtttaaatca aaactggtga aactcaccca 840
gggattggct gagacgaaaa acatattctc aataaaccct ttagggaaat aggccaggtt 900
ttcaccgtaa cacgccacat cttgcgaata tatgtgtaga aactgccgga aatcgtcgtg 960
gtattcactc cagagcgatg aaaacgtttc agtttgctca tggaaaacgg tgtaacaagg 1020
gtgaacacta tcccatatca ccagctcacc gtctttcatt gccatacgta attccggatg 1080
agcattcatc aggcgggcaa gaatgtgaat aaaggccgga taaaacttgt gcttattttt 1140
ctttacggtc tttaaaaagg ccgtaatatc cagctgaacg gtctggttat aggtacattg 1200
agcaactgac tgaaatgcct caaaatgttc tttacgatgc cattgggata tatcaacggt 1260
ggtatatcca gtgatttttt tctccatttt agcttcctta gctcctgaaa atctcgacaa 1320
ctcaaaaaat acgcccggta gtgatcttat ttcattatgg tgaaagttgg aacctcttac 1380
gtgccgatca acgtctcatt ttcgccaaaa gttggcccag ggcttcccgg tatcaacagg 1440
gacaccagga tttatttatt ctgcgaagtg atcttccgtc acaggtaggc gcgccgaagt 1500
tcctatactt tctagagaat aggaacttcg gaataggaac taaggaggat attcatatgg 1560
accatggcta attcccatgt cagccgttaa gcttctttgc cggatggtgg tcggcttcga 1620
aaggtaaaat ttctcattaa aaaaccgggc attgcccggt ttttttacgc ttattgatga 1680
cgcttacgaa gattgtcgat cacggtggtg aggttgagat cctgatcctg caacagcacc 1740
agcaggtggt acatcaaatc agacgcttca ttggttaatt caaaacgatc attgacggtg 1800
gccgccagcg cggtttctac accttcttcg ccaacttttt gcgcaatacg tttggtaccg 1860
ctggcgtaca gtttcgccgt gtaagagctg gccggatcgg cggttttgcg ctctgccagt 1920
agctgctcca gttgatacag gaataaccac tgatggctgg cgtcgccaaa gcagctgctg 1980
gtacctttgt ggcaggtcgg cccgacaggg tttgccagca ccagcagtgt atcgttgtcg 2040
caatctggcg caatgctgac gacattcagc acatggcctg aggtttcgcc tttggtccat 2100
aa 2102

<210> SEQ ID NO 12
<211> LENGTH: 2549
<212> TYPE: DNA
<213> ORGANISM: Artificial Sequence
<220> FEATURE:
<223> OTHER INFORMATION: linear targeting DNA fragment 2 containing a kan gene

<400> SEQUENCE: 12
ggatccaggc tttgactatg tggatgtgtt accgcgcatg agcctggagg aggtcgccag 60
agtgctggct ggcgcaaaat ttgtcgtatc ggttgatacc ggcctgagcc atctttccgc 120
ggcgctcgac agaccgaata ttacgctata tggcccaacg gaccctgggt taattggagg 180
ttatgggaag aaccaaatgg catgctgctc accagaacaa aacctggcga atttagatgc 240
cacaagcgta tttggaaaga ttcattaaag agactctgtc tcatcccaaa cctattgtgg 300
agaaaagatg ctaaccacat cattaacgtt aaataaagag aaatggaagc cgatctggaa 360
taaagcgctg gtttttcttt ttgttgccac gtattttctg gatggtatta cgcgttataa 420
acatttgata atcatactta tggttatcac cgcgatttat caggtctcac gctcaccgaa 480
aagtttcccc cctcttttca aaaatagcgt attttatagc gtagcagtat tatcattaat 540
ccttgtttat tccatactca tatcgccaga tgtcgacgtg taggctggag ctgcttcgaa 600
gttcctatac tttctagaga ataggaactt cggaatagga acttcaagat cccctcacgc 660

-continued

```
tgccgcaagc actcagggcg caagggctgc taaaggaagc ggaacacgta gaaagccagt    720

ccgcagaaac ggtgctgacc ccggatgaat gtcagctact gggctatctg gacaagggaa    780

aacgcaagcg caaagagaaa gcaggtagct tgcagtgggc ttacatggcg atagctagac    840

tgggcggttt tatggacagc aagcgaaccg gaattgccag ctggggcgcc ctctggtaag    900

gttgggaagc cctgcaaagt aaactggatg gctttcttgc cgccaaggat ctgatggcgc    960

aggggatcaa gatctgatca agagacagga tgaggatcgt ttcgcatgat tgaacaagat   1020

ggattgcacg caggttctcc ggccgcttgg gtggagaggc tattcggcta tgactgggca   1080

caacagacaa tcggctgctc tgatgccgcc gtgttccggc tgtcagcgca ggggcgcccg   1140

gttctttttg tcaagaccga cctgtccggt gccctgaatg aactgcagga cgaggcagcg   1200

cggctatcgt ggctggccac gacgggcgtt ccttgcgcag ctgtgctcga cgttgtcact   1260

gaagcgggaa gggactggct gctattgggc gaagtgccgg ggcaggatct cctgtcatct   1320

caccttgctc ctgccgagaa agtatccatc atggctgatg caatgcggcg gctgcatacg   1380

cttgatccgg ctacctgccc attcgaccac caagcgaaac atcgcatcga gcgagcacgt   1440

actcggatgg aagccggtct tgtcgatcag gatgatctgg acgaagagca tcaggggctc   1500

gcgccagccg aactgttcgc caggctcaag gcgcgcatgc ccgacggcga ggatctcgtc   1560

gtgacccatg gcgatgcctg cttgccgaat atcatggtgg aaaatggccg cttttctgga   1620

ttcatcgact gtggccggct gggtgtggcg gaccgctatc aggacatagc gttggctacc   1680

cgtgatattg ctgaagagct tggcggcgaa tgggctgacc gcttcctcgt gctttacggt   1740

atcgccgctc ccgattcgca gcgcatcgcc ttctatcgcc ttcttgacga gttcttctga   1800

gcgggactct ggggttcgaa atgaccgacc aagcgacgcc caacctgcca tcacgagatt   1860

tcgattccac cgccgccttc tatgaaaggt tgggcttcgg aatcgttttc cgggacgccg   1920

gctggatgat cctccagcgc ggggatctca tgctggagtt cttcgcccac cccagcttca   1980

aaagcgctct gaagttccta tactttctag agaataggaa cttcggaata ggaactaagg   2040

aggatattca tatggaccat ggctaattcc cataagcttt agtgcaggca tattgggtct   2100

ggcgagcctg gcctatttat atggtgctat catcagggaa acagccagct ctaccttcag   2160

gaaagtagag ataagcccct acaatgctca tctcttgcta tttttatctt tcgtcggttt   2220

ttatatcgtt cgtggcaatt ttgaacaggt cgatattgct caaattggta tcattaccgg   2280

ttttctgctg gcgctaagaa atagataaaa aacgcgctga tacttattac ggtatcagcg   2340

cgttttccat catcaggact caatcactta tcaaaccagt ttttcatttg ttcctcgaaa   2400

cgctgcgcta cattttccca actgtatttt gaaaacacca gggattttgc tttttcggca   2460

atctggtggc gttccttatc agcaagcgca cggttaatat cattaattat actgtcgctc   2520

gacataggtt ctgcgaggtg atactcgag                                     2549
```

<210> SEQ ID NO 13
<211> LENGTH: 87
<212> TYPE: DNA
<213> ORGANISM: Artificial Sequence
<220> FEATURE:
<223> OTHER INFORMATION: Neisseria meningitidis pilin PilE

<400> SEQUENCE: 13

```
agcgccgtga ccgagtacta tctgaaccat ggcgagtggc cgggtaataa caccagcgcc     60

ggcgtggcca caagcagtga gatcaag                                         87
```

<210> SEQ ID NO 14
<211> LENGTH: 29
<212> TYPE: PRT
<213> ORGANISM: Artificial Sequence
<220> FEATURE:
<223> OTHER INFORMATION: Neisseria meningitidis pilin PilE

<400> SEQUENCE: 14

```
Ser Ala Val Thr Glu Tyr Tyr Leu Asn His Gly Glu Trp Pro Gly Asn
1               5                   10                  15

Asn Thr Ser Ala Gly Val Ala Thr Ser Ser Glu Ile Lys
            20                  25
```

<210> SEQ ID NO 15
<211> LENGTH: 58
<212> TYPE: DNA
<213> ORGANISM: Artificial Sequence
<220> FEATURE:
<223> OTHER INFORMATION: 50973 cld cat 5' primer
<220> FEATURE:
<221> NAME/KEY: misc_feature
<222> LOCATION: (1)..(38)
<223> OTHER INFORMATION: cld homologous arm

<400> SEQUENCE: 15

```
ccagcttcat cctttttta gttagggtat ctatgacaag cgattgtgta ggctggag       58
```

<210> SEQ ID NO 16
<211> LENGTH: 60
<212> TYPE: DNA
<213> ORGANISM: Artificial Sequence
<220> FEATURE:
<223> OTHER INFORMATION: 50973 cld cat 3' primer
<220> FEATURE:
<221> NAME/KEY: misc_feature
<222> LOCATION: (1)..(34)
<223> OTHER INFORMATION: cld homologous arm

<400> SEQUENCE: 16

```
cctttcgaag ccgaccacca tccggcaaag aagctaatta acggctgaca tgggaattag     60
```

<210> SEQ ID NO 17
<211> LENGTH: 30
<212> TYPE: DNA
<213> ORGANISM: Artificial Sequence
<220> FEATURE:
<223> OTHER INFORMATION: 50973 cld up 5' primer

<400> SEQUENCE: 17

```
cagttgctgg ctaattatca gtcagtgcct                                      30
```

<210> SEQ ID NO 18
<211> LENGTH: 34
<212> TYPE: DNA
<213> ORGANISM: Artificial Sequence
<220> FEATURE:
<223> OTHER INFORMATION: 50973 cld up 3' primer

<400> SEQUENCE: 18

```
gtcatagata ccctaactaa aaaaaggatg aagc                                 34
```

<210> SEQ ID NO 19
<211> LENGTH: 30
<212> TYPE: DNA
<213> ORGANISM: Artificial Sequence
<220> FEATURE:
<223> OTHER INFORMATION: 50973 cld down 5' primer

<400> SEQUENCE: 19
ttctttgccg gatggtggtc ggcttcgaaa 30

<210> SEQ ID NO 20
<211> LENGTH: 30
<212> TYPE: DNA
<213> ORGANISM: Artificial Sequence
<220> FEATURE:
<223> OTHER INFORMATION: 50973 cld down 3' primer

<400> SEQUENCE: 20
ttatggacca aaggcgaaac ctcaggccat 30

<210> SEQ ID NO 21
<211> LENGTH: 36
<212> TYPE: DNA
<213> ORGANISM: Artificial Sequence
<220> FEATURE:
<223> OTHER INFORMATION: 66tac 5' primer

<400> SEQUENCE: 21
aaaatctaga gcgccgacat cataacggtt ctggca 36

<210> SEQ ID NO 22
<211> LENGTH: 34
<212> TYPE: DNA
<213> ORGANISM: Artificial Sequence
<220> FEATURE:
<223> OTHER INFORMATION: 66tac 3' primer

<400> SEQUENCE: 22
ttttctcgag cgttcaccga caaacaacag ataa 34

<210> SEQ ID NO 23
<211> LENGTH: 26
<212> TYPE: DNA
<213> ORGANISM: Artificial Sequence
<220> FEATURE:
<223> OTHER INFORMATION: 73waaLu1 primer
<220> FEATURE:
<221> NAME/KEY: misc_feature
<222> LOCATION: (3)..(8)
<223> OTHER INFORMATION: recognition site for restriction enzyme
digestion

<400> SEQUENCE: 23
cgggatccag gctttgacta tgtgga 26

<210> SEQ ID NO 24
<211> LENGTH: 27
<212> TYPE: DNA
<213> ORGANISM: Artificial Sequence
<220> FEATURE:
<223> OTHER INFORMATION: 73waaLu2 primer
<220> FEATURE:
<221> NAME/KEY: misc_feature
<222> LOCATION: (3)..(8)
<223> OTHER INFORMATION: recognition site for restriction enzyme
digestion

<400> SEQUENCE: 24
gcgtcgacat ctggcgatat gagtatg 27

<210> SEQ ID NO 25
<211> LENGTH: 26
<212> TYPE: DNA
<213> ORGANISM: Artificial Sequence
<220> FEATURE:
<223> OTHER INFORMATION: 73waaLd1 primer
<220> FEATURE:
<221> NAME/KEY: misc_feature
<222> LOCATION: (3)..(8)
<223> OTHER INFORMATION: recognition site for restriction enzyme digestion

<400> SEQUENCE: 25
ccaagcttta gtgcaggcat attggg 26

<210> SEQ ID NO 26
<211> LENGTH: 26
<212> TYPE: DNA
<213> ORGANISM: Artificial Sequence
<220> FEATURE:
<223> OTHER INFORMATION: 73waaLd2 primer
<220> FEATURE:
<221> NAME/KEY: misc_feature
<222> LOCATION: (3)..(8)
<223> OTHER INFORMATION: recognition site for restriction enzyme digestion

<400> SEQUENCE: 26
ccctcgagta tcacctcgca gaacct 26

<210> SEQ ID NO 27
<211> LENGTH: 19
<212> TYPE: DNA
<213> ORGANISM: Artificial Sequence
<220> FEATURE:
<223> OTHER INFORMATION: 73waaLw1 primer

<400> SEQUENCE: 27
aacaccggat tacggataa 19

<210> SEQ ID NO 28
<211> LENGTH: 18
<212> TYPE: DNA
<213> ORGANISM: Artificial Sequence
<220> FEATURE:
<223> OTHER INFORMATION: 73waaLw2 primer

<400> SEQUENCE: 28
tgcatggtgg ctgtagaa 18

<210> SEQ ID NO 29
<211> LENGTH: 18
<212> TYPE: DNA
<213> ORGANISM: Artificial Sequence
<220> FEATURE:
<223> OTHER INFORMATION: 73waaLn1 primer

<400> SEQUENCE: 29
agaaacggtt gcgaaaat 18

<210> SEQ ID NO 30
<211> LENGTH: 18
<212> TYPE: DNA
<213> ORGANISM: Artificial Sequence
<220> FEATURE:
<223> OTHER INFORMATION: 73waaLn2 primer

<400> SEQUENCE: 30
atagccgtag cccttgat 18

<210> SEQ ID NO 31

-continued

<211> LENGTH: 28
<212> TYPE: DNA
<213> ORGANISM: Artificial Sequence
<220> FEATURE:
<223> OTHER INFORMATION: Kan1 primer

<400> SEQUENCE: 31
gcgtcgacgt gtaggctgga gctgcttc 28

<210> SEQ ID NO 32
<211> LENGTH: 28
<212> TYPE: DNA
<213> ORGANISM: Artificial Sequence
<220> FEATURE:
<223> OTHER INFORMATION: Kan2 primer

<400> SEQUENCE: 32
ccaagcttat gggaattagc catggtcc 28

<210> SEQ ID NO 33
<211> LENGTH: 34
<212> TYPE: DNA
<213> ORGANISM: Artificial Sequence
<220> FEATURE:
<223> OTHER INFORMATION: 223tac-box5' primer

<400> SEQUENCE: 33
atcgagatct actgcataat tcgtgtcgct caag 34

<210> SEQ ID NO 34
<211> LENGTH: 34
<212> TYPE: DNA
<213> ORGANISM: Artificial Sequence
<220> FEATURE:
<223> OTHER INFORMATION: 223tac-box3' primer

<400> SEQUENCE: 34
atcgagatct gtctcatgag cggatacata tttg 34

*SALMONELLA PARATYPHI A* WITH AN O-ANTIGEN HAVING AN EXTENDED CARBOHYDRATE CHAIN AND USE THEREOF

REFERENCE TO SEQUENCE LISTING SUBMITTED ELECTRONICALLY

The content of the electronically submitted substitute sequence listing, file name 3932_0030001_SeqListing.txt, size 38,864 bytes; and date of creation Aug. 22, 2017, filed herewith, is incorporated herein by reference in its entirety.

TECHNICAL FIELD

The present invention relates to the field of biotechnology, and in particular, relates to a *Salmonella paratyphi* A with an O-Antigen having an extended carbohydrate chain and use thereof.

BACKGROUND ART

*Salmonella* spp. is a highly contagious gram-negative intestinal pathogen with strong endotoxin and invasiveness, belongs to intracellular bacteria, and can attach small intestinal mucosal to cause diseases such as enteric fever, gastroenteritis and septicemia, even severe intestinal bleeding or perforation. For most serotypes of *Salmonella*, their median infective doses are between $10^5$ and $10^8$, but in epidemic outbreaks, the infective doses are generally less than $10^3$ bacteria, sometimes even less than 100 bacteria. In Asian countries, especially in China, the proportion of intestinal diseases caused by *Salmonella paratyphi* A is increasing, and some studies find that there are 150 cases of *Salmonella paratyphi* A infection per 100 000 people per year.

At present, the main way to treat typhoid and paratyphoid is antibiotics, but with the emergence of drug-resistance, especially the emergence of multiple drug-resistant strains, conventional antibiotic treatment encounters a huge challenge, and immunization of relevant vaccines is an effective means of prevention. At present, the progresses of research and development for oral attenuated live vaccine against *Salmonella typhimurium*, Vi capsular polysaccharide vaccine and Vi polysaccharide-protein conjugate vaccine are rapid, and there are a variety of products listed, but these vaccines are not able to generate cross immunoprotection against *Salmonella paratyphi* A. Currently, there is not a vaccine against *Salmonella paratyphi* A that has been approved for listing.

CONTENTS OF THE INVENTION

One object of the present invention is to provide a recombinant strain.

The recombinant strain as provided by the present invention is obtained by introducing $cld_{LT2}$ gene encoding an enzyme controlling chain length of O-antigen of *Salmonella typhimurium* into *Salmonella paratyphi* A deficient in cld gene encoding an enzyme controlling chain length of O-antigen.

In the above recombinant strain, the enzyme controlling chain length of O-antigen of *Salmonella typhimurium* has an amino acid sequence with at least 90% identity to the amino acid sequence as shown in SEQ ID NO: 2;

the enzyme (also named as $Cld_{LT2}$) controlling chain length of O-antigen of *Salmonella typhimurium* has an amino acid sequence as shown in SEQ ID NO: 2;

the enzyme $Cld_{LT2}$ controlling chain length of O-antigen of *Salmonella typhimurium* has a coding sequence as shown in SEQ ID NO: 1.

In the above recombinant strain, *Salmonella paratyphi* A deficient in cld gene encoding an enzyme controlling chain length of O-antigen is obtained by knocking out cld gene via Red recombination technology, or by knocking out cld gene via homologous recombination, or by inserting an inactivated cld gene, or the cld deficient strain can be obtained by induced mutation; preferably, is obtained by knocking out cld gene via Red recombination technology.

In the above recombinant strain, *Salmonella paratyphi* A deficient in cld gene encoding an enzyme controlling chain length of O-antigen is obtained by a method comprising the following steps:

(1) preparing a linear targeting DNA fragment 1, which has a nucleotide sequence as shown in SEQ ID NO: 11, which contains a cat gene;

(2) transforming pKD46 plasmid into *Salmonella. paratyphi*, to obtain a recombinant strain designated as *S. paratyphi*/pKD46;

(3) inducing expression of Red recombination system in the *S. paratyphi*/pKD46 strain, and transforming the linear targeting DNA fragment 1 into the *S. paratyphi*/pKD46 strain, so that the linear targeting DNA fragment 1 replaces the cld gene in the *S. paratyphi*/pKD46 strain to obtain a recombinant strain designated as *S. paratyphi* cld::cat/pKD46;

(4) deleting the pKD46 plasmid from the *S. paratyphi* cld::cat/pKD46 strain, to obtain a recombinant strain designated as *S. paratyphi* cld::cat;

the *S. paratyphi* cld::cat is a *S. paratyphi* in which cld gene sequence is substituted with cat gene sequence;

(5) transforming plasmid pCP20 into the *S. paratyphi* cld::cat and deleting cat gene, to obtain a recombinant strain designated as *S. paratyphi* Δcld;

the *S. paratyphi* Acid is a cld gene-deleted *S. paratyphi.*

Another object of the present invention is to provide a method for extending carbohydrate chain length of O-antigen of *Salmonella paratyphi* A.

The method for extending carbohydrate chain length of O-antigen of *Salmonella paratyphi* A as provided in the present invention comprises the following steps: culturing the above recombinant strain to express the $cld_{LT2}$ gene, so that the recombinant strain synthesizes an O-antigen of which carbohydrate chain length is extended.

It is also an object of the present invention to provide an O-antigen.

The O-antigen provided by the present invention is prepared according to the method described above.

The use of the above-described O-antigen in the manufacture of a product for the prevention or prophylaxis of diseases caused by *Salmonella paratyphi* A is also within the scope of the present invention.

It is a further object of the present invention to provide an method for preparing a vaccine for the prevention and/or treatment of diseases caused by *Salmonella paratyphi* A via one-step bio-crosslinking.

The for preparing a vaccine for the prevention and/or treatment of diseases caused by *Salmonella paratyphi* A as provided in the present invention via one-step bio-crosslinking method comprises the steps of:

(1) inactivating cld gene encoding an enzyme controlling chain length of O-antigen of *Salmonella paratyphi* A and waaL gene encoding O-antigen ligase of *Salmonella paratyphi* A, to obtain a *Salmonella paratyphi* A with double deletion of cld gene and waaL gene;

(2) introducing a $cld_{LT2}$ gene encoding an enzyme controlling chain length of O-antigen of *Salmonella typhimurium*, a pglL gene encoding O-oligosaccharyltransferase of *Neisseria meningitidis* and a gene encoding recombinant fusion protein into the *Salmonella paratyphi* A with double deletion of cld gene and waaL gene, to obtain a recombinant strain;

(3) culturing the recombinant strain to obtain recombinant fusion protein with O-antigen-modified, and processing the recombinant fusion protein with O-antigen-modified to obtain the target vaccine.

In the above method, the *Salmonella paratyphi* A with double deletion of cld gene encoding an enzyme controlling chain length of O-antigen and waaL gene encoding O-antigen ligase can be obtain by knocking out cld gene and waaL gene via Red recombination technology, or by knocking out cld gene and waaL gene via homologous recombination, or by inserting an inactivated cld gene and waaL gene, or by obtaining a stain with deletion of cld and waaL genes by induced mutation; preferably, is obtained via Red recombination technology.

In the above method, the *Salmonella paratyphi* A with double deletion of cld gene encoding an enzyme controlling chain length of O-antigen and waaL gene encoding O-antigen ligase is constructed by a method comprising the following steps:

(1) preparing a linear targeting DNA fragment 2, which has a nucleotide sequence as shown in SEQ ID NO: 12, which contains a kan gene;

(2) transforming pKOBEG plasmid into the *S. paratyphi*Δcld strain, to obtain a recombinant strain designated as *S. paratyphi*Δcld/pKOBEG;

(3) inducing expression of Red recombination system in the *S. paratyphi*Δcld/pKOBEG strain, and transforming the linear targeting DNA fragment 2 into the *S. paratyphi*Δcld/pKOBEG strain, so that the linear targeting DNA fragment 2 replaces the waaL gene, in the *S. paratyphi*Δcld/pKOBEG strain to obtain a recombinant strain designated as *S. paratyphi*Δcld waal::kan/pKOBEG;

(4) deleting the pKOBEG plasmid from the *S. paratyphi*Δcld waal::kan/pKOBEG strain, to obtain a recombinant strain designated as *S. paratyphi*ΔcldwaaL::kan;

the *S. paratyphi*ΔcldwaaL::kan is a *S. paratyphi*Δcld in which waaL gene sequence is substituted with kan gene sequence;

(5) transforming plasmid pCP20 into the *S. paratyphi*ΔcldwaaL::kan and deleting kan gene, to obtain a recombinant strain designated as *S. paratyphi*ΔcldΔwaaL;

the *S. paratyphi*ΔcldΔwaaL is a *S. paratyphi* with deletion of cld gene and waaL gene.

In the above method, the recombinant fusion protein comprises a N-terminal signal peptide, a carrier protein, and a peptide fragment comprising a serine as an O-glycosylation site at position 63 of *Neisseria meningitidis* pilin PilE.

In the above method, the carrier protein is a non-toxic mutant of a bacterial toxin protein or a fragment of a bacterial toxin protein.

In the above method, the bacterial toxin protein is *Pseudomonas aeruginosa* exotoxin A, cholera toxin, diphtheria toxin or tetanus toxin.

In the above method, the non-toxic mutant of the bacterial toxin protein is a non-toxic mutant of *Pseudomonas aeruginosa* exotoxin A or a non-toxic mutant of diphtheria toxin; the fragment of the bacterial toxin protein is a B subunit of cholera toxin or a C protein of tetanus toxin.

In the above method, the carrier protein is specifically a non-toxic mutant of *Pseudomonas aeruginosa* exotoxin A or a B subunit of cholera toxin.

In the above method, the peptide fragment comprising a serine as an O-glycosylation site at position 63 of *Neisseria meningitidis* pilin PilE is a peptide fragment having an amino acid sequence as set forth in positions 45-73 of *Neisseria meningitidis* pilin PilE.

In the above method, the N-terminal signal peptide can be a signal peptide such as PelB, DsbA, STII, OmpA, PhoA, LamB, SpA, Enx, and the N-terminal signal peptide is specifically a DsbA signal peptide.

In the above method, the $cld_{LT2}$ gene encoding an enzyme controlling chain length of O-antigen of *Salmonella typhimurium*, the pglL gene encoding O-oligosaccharide transferase of *Neisseria meningitidis* and a gene encoding the recombinant fusion protein can be separately constructed into different recombinant expression vectors and introduced into the *Salmonella paratyphi* A with double deletion of cld and waaL, or can be constructed into the same recombinant expression vector and introduced into the *Salmonella paratyphi* A with double deletion of cld and waaL, or can also be introduced into the *Salmonella paratyphi* A with double deletion of cld and waaL via separately incorporating them into a host genome; the $cld_{LT2}$ gene encoding an enzyme controlling chain length of O-antigen of *Salmonella typhimurium*, the pglL gene encoding O-oligosaccharide transferase of *Neisseria meningitidis* and the gene encoding the recombinant fusion protein can be controlled by an inducible promoter, or controlled by a constitutive promoter.

In the above method, the $cld_{LT2}$ gene encoding an enzyme controlling chain length of O-antigen of *Salmonella typhimurium*, the pglL gene encoding O-oligosaccharide transferase of *Neisseria meningitidis* are specifically introduced into the *Salmonella paratyphi* A with double deletion of cld gene encoding an enzyme controlling chain length of O-antigen and waaL gene encoding O-antigen ligase via pETtac28-pglL-$cld_{LT2}$ recombinant expression vector.

In the above method, the gene encoding the recombinant fusion protein is specifically introduced into the *Salmonella paratyphi* A with double deletion of cld gene encoding an enzyme controlling chain length of O-antigen and waaL gene encoding O-antigen ligase via pMMB66EH-rCTB4573 recombinant expression vector or pMMB66EH-rEPA4573 recombinant expression vector or pMMB66EH-$rCTB4573_3$ recombinant expression vector.

In the above method, the pETtac28-pglL-$cld_{LT2}$ recombinant expression vector is constructed by a method comprising: using restriction endonucleases EcoR I and Hind III to perform double digestion of $cld_{LT2}$ gene encoding an enzyme controlling chain length of O-antigen of *Salmonella typhimurium* and the pMMB66EH vector, ligating to obtain a transition vector pMMB66EH-$cld_{LT2}$; using the transition vector pMMB66EH-$cld_{LT2}$ as template, amplifying to obtain an expression cassette of $cld_{LT2}$, using restriction endonuclease Xba I and Xho I to perform double digestion of the expression cassette of $cld_{LT2}$ and pET28a vector, ligating to obtain pETtac28-$cld_{LT2}$ vector; using restriction endonucleases EcoR I and Hind III to perform double digestion of O-oligosaccharide transferase gene pglL of *Neisseria meningitidis* and pKK223-3 vector, ligating to obtain pKK223-3-pglL vector; using pKK223-3-pglL vector as template, amplifying to obtain an expression cassette of PglL; using restriction endonuclease Bgl II to perform double digestion of the expression cassette of PglL and the pETtac28-cld$_{LT2}$ vector, ligating to obtain the pETtac28-pglL-cld$_{LT2}$ recombinant expression vector.

In the above method, the pMMB66EH-rEPA4573 recombinant expression vector is constructed by a method comprising: ligating the gene encoding fusion protein rEPA4573 of recombinant *Pseudomonas aeruginosa* exotoxin A into a multiple cloning site of pMMB66EH vector to obtain the pMMB66EH-rEPA4573 recombinant expression vector.

In the above method, the pMMB66EH-rCTB4573 recombinant expression vector is constructed by a method comprising: ligating the gene encoding fusion protein rCTB4573 of recombinant cholera toxin B subunit into a multiple cloning site of pMMB66EH vector to obtain the pMMB66EH-rCTB4573 recombinant expression vector.

In the above method, the pMMB66EH-rCTB4573$_3$ recombinant expression vector is constructed by a method comprising: ligating the gene encoding fusion protein rCTB4573$_3$ of recombinant cholera toxin B subunit into a multiple cloning site of pMMB66EH vector to obtain the pMMB66EH-rCTB4573$_3$ recombinant expression vector.

In the above method, the enzyme Cld$_{LT2}$ controlling chain length of O-antigen of *Salmonella typhimurium* has an amino acid sequence as shown in SEQ ID NO: 2; and gene encoding the enzyme controlling chain length of O-antigen of *Salmonella typhimurium* has a sequence as shown in SEQ ID NO: 1;

the *Neisseria meningitides* oligosaccharyltransferase pglL has an amino acid sequence as shown in SEQ ID NO: 8; the gene encoding *Neisseria meningitides* oligosaccharyltransferase pglL has a sequence as shown in SEQ ID NO: 7;

the fusion protein rEPA4573 of recombinant *Pseudomonas aeruginosa* exotoxin A has an amino acid sequence as shown in SEQ ID NO: 4; the Nos 1-19 from the N-terminal of the sequence shown in SEQ ID NO: 4 are of an amino acid sequence of the DsbA signal peptide; the amino acids at Nos 20-631 are of an amino acid sequence of the non-toxic mutant of *Pseudomonas aeruginosa* exotoxin A; the Nos 632-636 are of a flexible linker sequence; the amino acids at Nos 637-665 are of an amino acid sequence of a peptide at sites 45-73 of *Neisseria meningitidi* spilin PilE (NC_003112.2); the Nos 666-674 are of a flexible linker sequence and a 6×His tag sequence; the fusion protein rEPA4573 of recombinant *Pseudomonas aeruginosa* exotoxin A has a coding sequence as shown in SEQ ID NO: 3;

the fusion protein rCTB4573 of recombinant cholera toxin B subunit has an amino acid sequence as shown in SEQ ID NO: 6; the Nos 1-19 from the N-terminal of the sequence shown in SEQ ID NO: 6 are of an amino acid sequence of the DsbA signal peptide; the Nos 20-122 are of amino acid sequence of cholera toxin B subunit; the Nos 123-127 are of a flexible linker sequence; the Nos 128-156 are of an amino acid sequence of a peptide at sites 45-73 of *Neisseria meningitidis* pilin PilE (NC_003112.2); the Nos 157-166 are of a flexible linker and a 6×His tag sequence; the fusion protein rCTB4573 of recombinant cholera toxin B subunit has a coding sequence as shown in SEQ ID NO: 5;

the fusion protein rCTB4573$_3$ of recombinant cholera toxin B subunit has an amino acid sequence as shown in SEQ ID NO: 10; the Nos 1-19 from the N-terminal of the sequence shown in SEQ ID NO: 10 are of an amino acid sequence of the DsbA signal peptide; the Nos 20-122 are of amino acid sequence of cholera toxin B subunit; the Nos 123-127 are of a flexible linker sequence; the Nos 128-222 are of an amino acid sequence of 3 repetitive peptides of that at sites 45-73 of *Neisseria meningitidis* pilin PilE (NC_003112.2); the Nos 223-232 are of a flexible linker and a 6×His tag sequence; the fusion protein rCTB4573$_3$ of recombinant cholera toxin B subunit has a coding sequence as shown in SEQ ID NO: 9;

the peptide as set forth in amino acid position 45-73 of *Neisseria meningitidis* pilin PilE has an amino acid sequence as shown in SEQ ID NO: 14; and gene encoding the peptide has a sequence as shown in SEQ ID NO: 13.

The vaccines as prepared according to the above methods also fall into the protection scope of the present invention.

The uses of the vaccines in manufacture of a product for prophylaxis and/or treatment of a disease caused by *Salmonella paratyphi* A also fall into the protection scope of the present invention.

BEST MODELS FOR CARRYING OUT THE INVENTION

Figure 1:
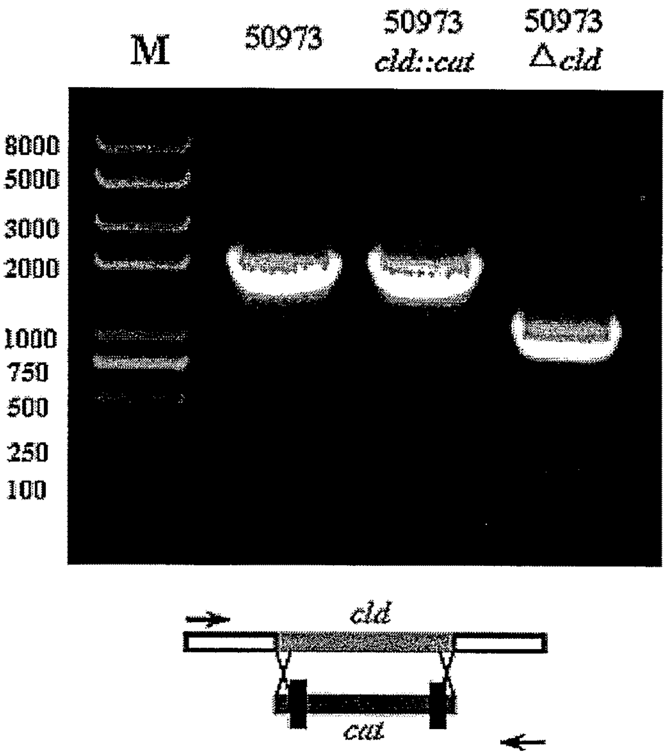
FIG. 1 shows a PCR identification diagram of *S. paratyphi* CMCC50973 with knockout of cld gene.

The experimental methods used in the following examples are conventional methods unless otherwise specified.

The materials, reagents and the like used in the following examples are commercially available, unless otherwise specified.

Experimental materials: *Salmonella paratyphi* A CMCC50973 strain (*Salmonella. paratyphi* CMCC50973), purchased from the China Medical Bacteria Deposit Management Center.

pET-22b plasmid, purchased from Novagen Corporation under catalog number 69744.

pKOBEG plasmid, disclosed in the literature "A rapid method for efficient gene replacement in the filamentous fungus *Aspergillus nidulans* [J]. Nucleic Acids Res. 2000 Nov. 15; 28 (22): E97", available for the public in the Institute of Bioengineering of the Academy of Military Medical Sciences of the Chinese People's Liberation Army; the plasmid is a temperature-sensitive plasmid with chloramphenicol resistance.

pKD3 plasmid, disclosed in the literature "Datsenko, K. A. and B. L. Wanner, One-step inactivation of chromosomal genes in *Escherichia coli* K-12 using PCR products. Proc Natl Acad Sci USA, 2000, 97(12): p. 6640-5."; available for the public in the Institute of Bioengineering of the Academy of Military Medical Sciences of the Chinese People's Liberation Army.

pKD46 plasmid, discloses in the literature "Datsenko, K. A. and B. L. Warmer, One-step inactivation of chromosomal genes in *Escherichia coli* K-12 using PCR products. Proc Natl Acad Sci USA, 2000, 97(12): p. 6640-5."; available for the public in the Institute of Bioengineering of the Academy of Military Medical Sciences of the Chinese People's Liberation Army. The replicons of the pKD46 plasmid are temperature sensitive, which would be disappeared during culture at 37° C., and this plasmid contains DNA encoding three recombinases for the Red recombination system, which is controlled by arabinose promoter.

pCP20 plasmid, disclosed in the literature "Datsenko, K. A. and B. L. Wanner, One-step inactivation of chromosomal genes in *Escherichia coli* K-12 using PCR products. Proc Natl Acad Sci USA, 2000, 97(12): p. 6640-5."; available for the public in the Institute of Bioengineering of the Academy of Military Medical Sciences of the Chinese People's Liberation Army. The replicons of the pCP20 plasmid are temperature sensitive, which be lost during culture at 42° C. The plasmid contains DNA encoding FLP recombinase, which is controlled by a thermo-sensitive promoter, and the expression of FLP recombinase is induced at 42° C., while the plasmid is lost.

Aluminum hydroxide adjuvant Rehydragel LV was purchased from General Chemical Company.

Example 1. Method for Extending Length of *Salmonella paratyphi* A O-Antigen Carbohydrate Chain I. Knocking Out cld Gene Encoding an Enzyme Controlling Chain Length of O-Antigen of *Salmonella paratyphi* A CMCC50973 Strain 1. Preparation of Linear Targeting DNA Fragment 1

1) Design of PCR Primer

The targeting fragment of the cld gene (sites 887812 to 888789) was designed according to the *S. paratyphi* ATCC9150 genome sequence (CP000026) published by GeneBank, and the cld gene of *Salmonella paratyphi* A CMCC50973 was knocked out. In the upstream and downstream of the cld gene, 500 bp fragments were cut out and used as the homologous arms, and the targeting fragment of chloramphenicol resistant gene containing 500 bp homologous sequence and FRT site at both ends was amplified by PCR. 50973cld up 5' and 50973cld down 3' were used to identify whether the cld gene was knocked out. The specific primer design was shown in Table 1.

TABLE 1

Primers used for knocking out cld gene of *Salmonella paratyphi A* CMCC50973 strain

| Name of primer | Primer sequence (5'→3') | Notes | Effect of primer pair |
|---|---|---|---|
| 50973 cld cat 5' | CCAGCTTCATCCTTTTTTTAGTTAGGGTATCTATGACAAGCGATTGTGTAGGCTGGAG (SEQ ID NO: 15) | Underlined part was cld homologous arm. | Amplifying to obtain chloramphenicol resistant gene fragments with cld upstream and downstream homologous arms. |
| 50973 cld cat 3' | CCTTTCGAAGCCGACCACCATCCGGCAAAGAAGCTAATTAACGGCTGACATGGGAATTAG (SEQ ID NO: 16) | | |
| 50973 cld up 5' | CAGTTGCTGGCTAATTATCAGTCAGTGCCT (SEQ ID NO: 17) | — | Amplifying cld primers of upstream and downstream homologous arms. |
| 50973 cld up 3' | GTCATAGATACCCTAACTAAAAAAAGGATGAAGC (SEQ ID NO: 18) | | |
| 50973 cld down 5' | TTCTTTGCCGGATGGTGGTCGGCTTCGAAA (SEQ ID NO: 19) | | |
| 50973 cld down 3' | TTATGGACCAAAGGCGAAACCTCAGGCCAT (SEQ ID NO: 20) | | |

2) Acquisition of Linear Targeting DNA Fragment 1

Using the plasmid pKD3 as template, primers 50973 cld cat 5' and 50973 cld cat 3' were used to amplify a chloramphenicol resistant gene fragment 50973 cld cat which had at both ends homologous arms 41 bp upstream and downstream of the cld gene and FRT site; using *Salmonella paratyphi* A CMCC50973 genomic DNA as template, amplification was performed by using 50973 cld up5' and 50973 cld up3' to obtain cld upstream 500 bp homologous arm 50973 cld up, while using 50973 cld down 5' and 50973 cld down 3' to obtained cld downstream 500 bp homologous arm 50973 cld down, and then the 3 fragments 50973 cld cat, 50973 cld up and 50973 cld down were fused by PCR to obtain linear targeting DNA fragment 1 (SEQ ID NO: 11).

PCR reaction system was of 50 μL, which comprised Q5 super-fidelity DNA polymerase 0.5 μL, 5× buffer 10 μL, template 1 μL, dNTP 4 μL, primer 2.5 μL, deionized water 29.411;

PCR reaction conditions: 98° C. 20 s; 98° C. 10 s, 55° C. 10 s, 72° C. 50 s, 30 cycles; 72° C. 5 min, to obtain the linear targeting DNA fragment 1 as shown in SEQ ID NO: 11. The product was separated by 1% agarose gel electrophoresis, the target strip was cut out from the gel, and the PCR product was recovered by using a DNA gel recovery kit. The procedure was carried out according to the instructions.

2. Acquisition of *Salmonella paratyphi* A (*S. paratyphi* CMCC50973Δcld) Deficient in cld Gene Encoding an Enzyme Controlling Chain Length of O-Antigen 1) Preparation of *S. paratyphi* CMCC50973/pKD46

(1) *S. paratyphi* CMCC50973 was inoculated in a LB liquid medium, incubated overnight at 37° C., transferred to LB liquid medium at 1:100, and incubated at 37° C. until $OD_{600}$ reached 0.6.

(2) Bacteria were collected by centrifugation, washed with autoclavation sterilized 10% glycerol (v/v) for four times, and finally were suspended with 400 μL of 10% glycerol, to obtain competent cells for electroporation, which were sub-packaged, ready to use.

(3) pKD46 plasmid was electroporated into the prepared *S. paratyphi* CMCC50973 competent cells, coated on a LB plates containing 100 μg/mL ampicillin, cultured at 30° C. overnight, to obtain positive clones as *S. paratyphi* CMCC50973/pKD46 strain.

2) Acquisition of *S. paratyphi* CMCC50973 cld::cat Strain (1) The above obtained *S. paratyphi* CMCC50973/pKD46 was cultured overnight at 30° C. and passed at 1:100 in a LB liquid medium containing ampicillin.

(2) When $OD_{600}$ was about 0.2, L-arabinose at a final concentration of 0.2% (w/v) was added to induce the expression of Red recombination system, and when $OD_{600}$ value was 0.6, *S. paratyphi* CMCC50973/pKD46 competent cells were prepared by the steps as described above.

(3) 10 μL of the linear targeting DNA fragment 1 obtained in the above Step 1 was taken and electroporated into the sub-packaged *S. paratyphi* CMCC50973/pKD46 competent cells.

(4) The cells were rapidly added to 1 mL of pre-cooled LB medium, resuscitated at 30° C. for about 2.5 h, and then coated on a LB plate containing 30 μg/mL chloramphenicol at a final concentration, and placed in a 30° C. incubator for culture overnight.

(5) The positive clones were screened, and subjected to PCR identification using primers 50973 cld cat 5' and 50973 cld cat 3', in which the wild-type bacteria could not be amplified to generate fragments, the cld gene was identified to have a size of 1100 bp after being substituted by cat gene. According to the PCR results, positive clones of *S. paratyphi* CMCC50973 cells in which the cld gene was replaced by the cat gene were screened out, to obtain the deletion mutant *S. paratyphi* CMCC50973 cld::cat/pKD46.

3) Acquisition of *S. paratyphi* CMCC50973Δcld Strain (1) The positive clone *S. paratyphi* CMCC50973 cld::cat/pKD46 was inoculated into a LB liquid medium containing 30 μg/mL chloramphenicol, cultured and passed at 37° C. for three times (cultured for 12 h each time), to remove pKD46 plasmid, so as to obtain *S. paratyphi* CMCC50973 cld::cat strain.

(2) The *S. paratyphi* CMCC50973 cld::cat as prepared according to the above method was used for electroporation of the competent cells, and plasmid pCP20 was electroporated into *S. paratyphi* CMCC50973 cld::cat competent cells, and then coated with a LB plate containing ampicillin, so as to obtain *S. paratyphi* CMCC50973 cld::cat/pCP20 strain.

(3) *S. paratyphi* CMCC50973 cld::cat/pCP20 monoclones were picked and placed in a LB liquid medium, incubated at 30° C. until $OD_{600}$ was about 0.6, and transferred and cultured at 42° C. overnight.

(4) The bacterial solution cultured overnight at 42° C. was streaked on a LB plate, and monoclones were picked out on LB plates and LB plates containing chloramphenicol. The monoclones that grew on the LB plates but did not grow on chloramphenicol-containing LB plates were chosen, and subjected to PCR identification by using primers 50973 cld up 5' and 50973 cld down 3'. The PCR identification showed the size of wild *S. paratyphi* CMCC50973 fragment was 2028 bp, while the size after knockout of the cld gene was 1100 bp. The results of the PCR identification were shown in FIG. 1. The positive clone was named *S. paratyphi* CMCC50973Δcld.

II. Acquisition and Phenotype Identification of O-Antigen Carbohydrate Chain-Extended *Salmonella paratyphi* A 1. Construction of a Vector Expressing $cld_{LT2}$ Gene Encoding an Enzyme Controlling Chain Length of O-Antigen of *Salmonella typhimurium*

The DNA sequence as shown in SEQ ID NO: 1 was synthesized according to the nucleotide sequence of cld gene (GeneBank No.: NC_003197.1, position 2156832 to 2157815) encoding an enzyme controlling chain length of O-antigen of *Salmonella typhimurium*, and this gene was named as $cld_{LT2}$. The enzyme controlling chain length of O-antigen has an amino acid sequence as shown in SEQ ID NO: 2, and the $cld_{LT2}$ gene encoding the enzyme has a sequence as shown in SEQ ID NO: 1.

The synthesized $cld_{LT2}$ gene was digested with EcoRI and Hind III, linked into pMMB66EH expression vector (purchased from ATCC, ATCC37620), to construct transition vector pMMB66EH-$cld_{LT2}$, the primers 66tac 5' and 66tac 3' were designed by using pMMB66EH-$cld_{LT2}$ as template, the expression cassette carrying $cld_{LT2}$ gene was amplified, and linked to pET28a (purchased from Novagen) between restriction enzyme cutting sites of Xba I and XhoI, so as to construct expression vector pETtac28-$cld_{LT2}$. The primers were as follows:

```
                                         (SEQ ID NO: 21)
66tac 5': AAAATCTAGAGCGCCGACATCATAACGGTTCTGGCA;

                                         (SEQ ID NO: 22)
66tac 3': TTTTCTCGAGCGTTCACCGACAAACAACAGATAA.
```

The sequencing results showed that the sequence as shown in SEQ ID NO: 1 was inserted between the restriction enzyme cutting sites of Xba I and Xho I in the pET28a vector, which indicated the vector was correct.

2. *Salmonella paratyphi* A LPS Length Detection

The above-prepared *S. paratyphi* CMCC50973Δcld electroporation competent cells were electroporated with the above-obtained pETtac28-$cld_{LT2}$, coated on kanamycin-containing LB plates, and positive clones were picked and cultured at 37° C. When $OD_{600}$ was about 0.6, IPTG with a final concentration of 1 mM was added to induce expression of $cld_{LT2}$ gene.

After 10 h of induction, 1 mL of culture was taken and the cells were collected by centrifugation, washed with PBS once, and 100 μL of lysis buffer (2 mL of 10% SDS, 0.4 mL of 2-mercaptoethanol, 1 mL of 100% glycerol, 5 mL of 2M Tris-HCL pH 6.8, 20 μL of 10% bromophenol blue, 1.6 mL of $ddH_2O$) was added and fully mixed, heated with boiling water for 10 min, added with 4 μL of 20 mg/mL of proteinase K, reacted at 60° C. for 1-2 h, 15 μL of product was taken for loading and performing SDS-PAGE, in which the separation gel was 15%, the concentrated gel was 4%, and the electrophoresis was ceased after the bromophenol blue gel exuded for 30 minutes.

The above-mentioned polyacrylamide gel was placed in an immobilized solution overnight, added with a sensitizing solution and reacted for 30 min, washed with deionized water 3 times, 15 min per time, added a silver nitrate solution and reacted for 20 min, washed twice with deionized water, 1 min per time, add with a developer solution for color development, the reaction was finally terminated, and the product was washed with deionized water. At the same time, the wild strain of *S. paratyphi* CMCC50973 was used as control.

Figure 2:
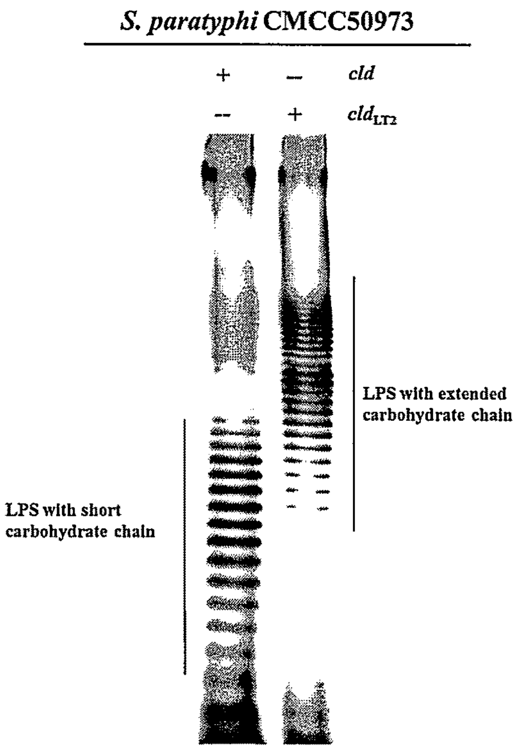
FIG. 2 shows a silver staining diagram of LPS before and after *S. paratyphi* CMCC50973 cld gene is replaced.

The results were showed in FIG. 2, in which the result of silver staining test showed that the LPS of the wild *S. paratyphi* CMCC50973 was distributed in the lower molecular weight region, while when the cld gene thereof was replaced by $cld_{LT2}$, relatively concentrated LPS stripes appeared in the higher molecular weight region, which indicated that by replacing the cld gene of *S. paratyphi* CMCC50973 with $cld_{LT2}$, the O-antigen carbohydrate chain thereof was significantly extended.

Example 2. *Salmonella paratyphi* A O-Antigen-Recombinant Fusion Protein Conjugate Vaccine as Prepared by One-Step Bio-Crosslinking Method and Uses Thereof I. Construction of O-Antigen Ligase Gene waaL Deficient *Salmonella paratyphi* A (I) Preparation of Linear Targeting DNA Fragment 2

1. Design and Synthesis of PCR Primers

By referring to the waaL gene (GeneBank No. CP000026, sites 3696236-3697450) in the whole genome sequence (NC_006511) of the *Salmonella paratyphi* A 50973 strain (*S. paratyphi* CMCC50973) and its upstream and downstream sequences, a pair of primers was designed for each of upstream (5' end) and downstream (3' end) of the waaL gene, namely 73waaLu1/73 waaLu2 and 73waaLd1/73waaLd2. For ease of manipulation, the restriction sites BamH I and Sal I were added to the primer ends of the upstream homologous arm up, and the restriction sites Hind III and Xho I were added to the primer ends of the downstream homologous arm down. In the meantime, besides the waaL gene upstream and downstream homologous arms on the genome, a pair of primers (73waaLw1/73waaLw2), a pair of internal detection primers (73waaLn1/73waaLn2) and a pair of kan gene primers (Kan1/Kan2) were designed for simultaneous sequencing and verification, in order to test whether the mutants were constructed successfully. The above-mentioned primers had sequences as shown in Table 2 (the underlined sequences were recognition sites for restriction enzyme digestion).

TABLE 2

Sequences of primers

| Primer | Sequence (5'→3') | Use |
|---|---|---|
| 73waaLu1 | CGGGATCCAGGCTTTGACTATGTGGA (SEQ ID NO: 23) | Amplifying up fragment |
| 73waaLu2 | GCGTCGACATCTGGCGATATGAGTATG (SEQ ID NO: 24) | |
| 73waaLd1 | CCAAGCTTTAGTGCAGGCATATTGGG (SEQ ID NO: 25) | Amplifying down fragment |
| 73waaLd2 | CCCTCGAGTATCACCTCGCAGAACCT (SEQ ID NO: 26) | |
| 73waaLw1 | AACACCGGATTACGGATAA (SEQ ID NO: 27) | Identifying mutants |
| 73waaLw2 | TGCATGGTGGCTGTAGAA (SEQ ID NO: 28) | |
| 73waaLn1 | AGAAACGGTTGCGAAAAT (SEQ ID NO: 29) | Identifying mutants |
| 73waaLn2 | ATAGCCGTAGCCCTTGAT (SEQ ID NO: 30) | |
| Kan1 | GCGTCGACGTGTAGGCTGGAGCTGCTTC (SEQ ID NO: 31) | Identifying mutants |
| Kan2 | CCAAGCTTATGGGAATTAGCCATGGTCC (SEQ ID NO: 32) | |

2. Construction of Linear Targeting DNA Fragment 2

1) Using the genomic DNA of *Salmonella paratyphi* A 50973 as template, the upstream and downstream homologous arms, up fragment and down fragment, of the waaL gene were amplified by 73waaLu1/73waaLu2 and 73waaLd1/73waaLd2, respectively. The PCR procedures were as follows: 94° C. 10 min; 94° C. 30 s, 50° C. 30 s, 72° C. 30 s, 30 cycles; 72° C. 10 min.

2) Construction of pETKan

The kan gene fragment represented by the nucleotide sequence at sites 578-2073 in SEQ ID NO: 12 was artificially synthesized, and the kan gene fragment and pET-22b plasmid were digested with the restriction enzymes SalI and Hind IIII, and a recombinant plasmid was obtained after ligating, and named as pETKan. The pETKan was sequenced and the results were correct.

3) The up fragment was doubly digested with restriction endonucleases BamH I and SalI to obtain a gene fragment 1; the plasmid pETKan was doubly digested with restriction endonucleases BamH I and Sal I to obtain a vector large fragment 1; and the gene fragment 1 was ligated with the vector large fragment 1 to obtain an intermediate vector 1;

the down fragment was doubly digested with restriction endonuclease Hind III and Xho I to obtain a gene fragment 2; the intermediate vector 1 was doubly digested with restriction endonuclease Hind III and Xho I to obtain a vector large fragment 2; and the gene fragment 2 was ligated with the vector large fragment 2 to obtain an intermediate vector 2.

4) The intermediate vector 2 was doubly digested with restriction endonucleases BamH I and Xho I to obtain the desired targeting DNA fragment that had homologous arms at both sides and contained the kan gene in the middle part, and the fragment has a nucleotide sequence as shown in SEQ ID NO: 12. In the SEQ ID NO: 12, as counting from the 5' end, the nucleotides at sites 7-571 were the up fragment, the nucleotides at sites 578-2073 were the kan gene, and the nucleotides at sites 2080-2543 were the down fragment.

A linear targeting DNA fragment 2 (SEQ ID NO: 12) with a concentration of up to 300 ng/μL was obtained by further PCR amplification of the target fragment by using the DNA fragment shown in SEQ ID NO: 12 as template and 73waaLu1 and 73waaLd2 as primers.

(II) Construction of *S. paratyphi* CMCC50973/pKOBEG

Since the pKOBEG plasmid contained the various enzymes required to encode the λ-Red recombination system, the pKOBEG plasmid was electroporated into *S. paratyphi* CMCC50973 competent cells, coated to chloramphenicol resistant (pKOBEG plasmid resistance, chloramphenicol) LB plate, and cultured at 30° C. overnight to obtain a positive clone, which was named as *S. paratyphi* CMCC50973/pKOBEG strain.

(III) Using Linear Targeting DNA Fragment 2 to Electroporate *S. paratyphi* CMCC50973/pKOBEG 1. *S. paratyphi* CMCC50973/pKOBEG was inoculated to a low salt LB medium containing chloramphenicol in a final concentration of 30 μg/mL and cultured overnight at 30° C., then passaged to a low salt LB liquid medium at a volume ratio of 1:100, and continuously cultured.

2. The culture medium in Step 1 was added with L-arabinose at a final concentration of 1 mmol/L at 1 hour before the $OD_{600}$ value reached 0.6, so as to induce the expression of the Red recombination system.

3. When the $OD_{600}$ value of the culture medium in step 2 reached 0.6, 5 μL of the 300 ng/μL linear targeting DNA fragment 2 as prepared in step (I) was taken and used to electroporate and transform *S. paratyphi* CMCC50973/pKOBEG.

4. 1 mL of pre-cooled low salt LB liquid medium was rapidly added to the transformed cells, resuscitation was performed at 30° C. for about 2.5 hours, and then the medium was coated on LB plates containing kanamycin at a concentration of 50 μg/mL, placed in 30° C. incubator and cultured overnight, and positive clones were screened out.

5. The positive clones were inoculated into a liquid LB medium (with kanamycin resistance at a concentration of 50 μg/mL), cultured and passaged twice at 42° C. (12 hours each time) to remove pKOBEG plasmid, and finally obtain a mutant with kanamycin resistance waaL deletion, named *S. paratyphi* CMCC50973 waaL::kan.

(IV) The plasmid pCP20 coding FRT site-specific recombinase was electroporated and transferred into *S. paratyphi* CMCC50973waaL::kan, cultured at 30° C. on a LB plate that contained chloramphenicol at a concentration of 50 μg/mL and was free of kanamycin, positive clones of $Cm^rKm^s$ (chloramphenicol resistant, Kanamycin sensitive) were screened out.

(V) The positive clones screened out in step (IV) were transferred into a liquid LB and cultured at 42° C. for 12 h to obtain a mutant with deletion of target genes that did not contain kanamycin and plasmid pCP20, which were named as *S. paratyphi* CMCC50973ΔwaaL, so that *Salmonella paratyphi* A with deletion of waaL gene was obtained.

II. Construction of *Salmonella paratyphi* A with Deletion of waaL Gene and cld Gene (I) Preparation of Linear Targeting DNA Fragment 2

The steps were the same of the above step (I).

(II) Construction of *S. paratyphi* CMCC50973Δcld/pKOBEG

Since the pKOBEG plasmid contained the various enzymes required to encode the λ-Red recombination system, the pKOBEG plasmid was electroporated and transformed into *S. paratyphi* CMCC50973Δcld competent cells, and coated a LB plate with chloramphenicol resistance (pKOBEG plasmid resistance, chloramphenicol), cultured at 30° C. overnight to give a positive clone named *S. paratyphi* CMCC50973Δcld/pKOBEG strain.

(III) Using Linear Targeting DNA Fragment 2 to Electroporate *S. paratyphi* CMCC50973Δcld/pKOBEG 1. *S. paratyphi* CMCC50973Δcld/pKOBEG was inoculated to a low salt LB liquid culture medium containing chloramphenicol at a final concentration of 30 μg/mL and cultured at 30° C. overnight, and then passaged to a low salt LB liquid medium at a volume ratio of 1:100, and continuously cultured.

2. The culture medium in Step 1 was added with L-arabinose at a final concentration of 1 mmol/L at 1 hour before the $OD_{600}$ value reached 0.6, so as to induce the expression of the Red recombination system.

3. When the $OD_{600}$ value of the culture medium in step 2 reached 0.6, 5 μL of the 300 ng/μL linear targeting DNA fragment 2 as prepared in step (I) was taken and used to electroporate and transform *S. paratyphi* CMCC50973Δcld/pKOBEG.

4. 1 mL of pre-cooled low salt LB liquid medium was rapidly added to the transformed cells, resuscitation was performed at 30° C. for about 2.5 hours, and then the medium was coated on LB plates containing kanamycin at a concentration of 50 μg/mL, placed in 30° C. incubator and cultured overnight, and positive clones were screened out.

5. The positive clones were inoculated into a liquid LB medium (with kanamycin resistance at a concentration of 50 μg/mL), cultured and passaged twice at 42° C. (12 hours each time) to remove pKOBEG plasmid, and finally obtain a mutant with kanamycin resistance waaL deletion, named *S. paratyphi* CMCC50973ΔcldwaaL::kan.

(IV) The plasmid pCP20 coding FRT site-specific recombinase was electroporated and transferred into *S. paratyphi* CMCC50973ΔcldwaaL::kan, cultured at 30° C. on a LB plate that contained chloramphenicol at a concentration of 50 μg/mL and was free of kanamycin, positive clones of $Cm^rKm^s$ (chloramphenicol resistant, Kanamycin sensitive) were screened out.

(V) The positive clones screened out in step (IV) were transferred into a liquid LB and cultured at 42° C. for 12 h to obtain a mutant with deletion of target genes that did not contain kanamycin and plasmid pCP20, which were named as *S. paratyphi* CMCC50973ΔcldΔwaaL.

II. Molecular Identification of *S. paratyphi* CMCC50973ΔcldΔwaaL

Figure 8:
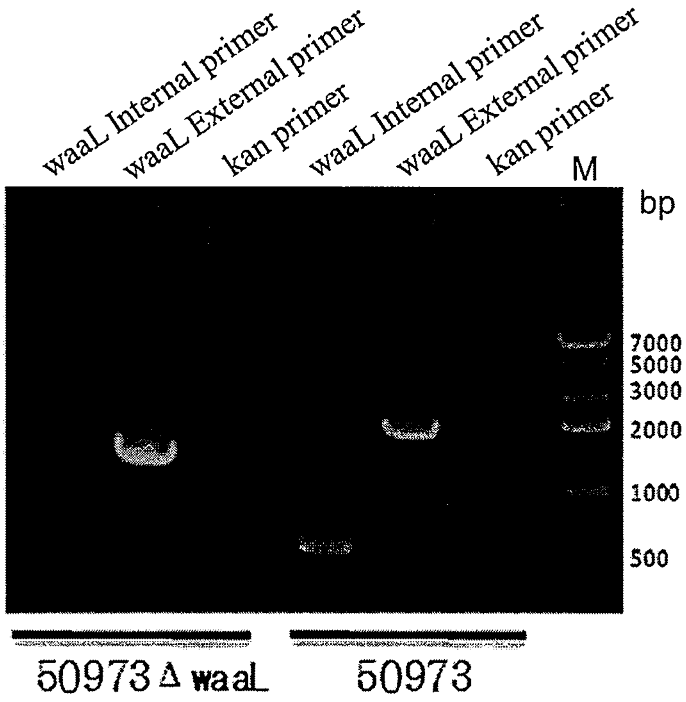
FIG. 8 shows a molecular identification of *S. paratyphi* CMCC50973ΔcldΔwaaL.

The genomic DNAs of *S. paratyphi* CMCC509730cld and *S. paratyphi* CMCC50973ΔcldΔwaaL were separately used as templates, and PCR identification was performed by separately using a pair of waaL internal primers (73 waaLn1/73 waaLn2), a pair of waaL external primers (73waaLw1/73waaLw2) and kan primers (kan1/kan2). The results are shown in FIG. 8; and in FIG. 8, 50973ΔwaaL represents *S. paratyphi* CMCC50973ΔcldΔwaaL; 50973 represents *S. paratyphi* CMCC50973Δcld.

The results showed that there was not a target strip when the PCR amplification was performed by using the genomic DNA of *S. paratyphi* CMCC50973ΔcldΔwaaL as template and waaL internal primers as primers; while there was a target strip when the PCR amplification was performed by using the genomic DNA of *S. paratyphi* CMCC50973Δcld as template and waaL internal primers as primers. Moreover, since the *S. paratyphi* CMCC50973ΔcldΔwaaL had knock-out of waaL gene, the target strip obtained when performing the PCR amplification by using the genomic DNA of *S. paratyphi* CMCC50973ΔcldΔwaaL as template and waaL external primers as primers was smaller than the strip obtained when performing PCR amplification by using the genomic DNA of *S. paratyphi* CMCC50973Δcld as template and waaL external primers as primers. As a result of the removal of the Kan resistance gene, there was not a target strip when the PCR amplification was performed by using the genomic DNA of *S. paratyphi* CMCC50973ΔcldΔwaaL as a template and the kan primer as a primer.

These results demonstrated the successful construction of the *Salmonella paratyphi* A 50973 mutant *S. paratyphi* CMCC50973ΔcldΔwaaL, which had waaL gene deletion and cld gene deletion.

III. Construction of Glycosylation Engineering *Salmonella paratyphi* A

1. Construction of rEPA4573 and rCTB4573 Expression Vectors

A recombinant *Pseudomonas aeruginosa* exotoxin A fusion protein (rEPA4573) was constructed according to the amino acid sequence of *Pseudomonas aeruginosa* exotoxin A (AE004091.2) published by GeneBank, in which its signal peptide (the first 25 amino acids) was replaced by DsbA signal peptide, its E at position 553 was deleted, in the meantime, the L at position 552 was mutated as V, and its C-terminal was fused with the polypeptide sequences shown in positions 45-73 amino acids (defined as Pla) of *Neisseria meningitidis* pilin PiLE (NC_003112.2) and 6×His tag. The amino acid sequence of the optimized rEPA4573 was shown in SEQ ID NO: 4, wherein the 1-19 positions were the amino acid sequence of the DsbA signal peptide; the amino acids at positions 20-631 were the amino acid sequence of non-toxic mutant of *Pseudomonas aeruginosa* toxin protein A; the amino acids 637-665 were the amino acid sequence of the polypeptide at 45-73 positions of *Neisseria meningitidis* pilin PiLE (NC_003112.2), and the amino acids 666-674 were flexible linker sequence and 6×His tag sequence; the optimized gene sequence of rEPA4573 was shown in SEQ ID NO: 3. The artificially synthesized rEPA4573 coding sequence was digested with EcoR I and Hind III, and ligated into pMMB66EH expression vector (ATCC, ATCC37620) to construct pMMB66EH-rEPA4573 vector.

Sequencing results showed that the sequence shown in SEQ ID NO: 3 was inserted between the EcoR I and Hind III cleavage sites of the pMMB66EH expression vector, indicating that the vector was correct.

The recombinant CTB fusion protein (rCTB4573) was constructed according to the amino acid sequence of cholera toxin B subunit (CTB) (X76390.1) published by GeneBank, in which its signal peptide (the first 21 amino acids) was replaced by the DsbA signal peptide, and the C-terminal of the recombinant fusion protein was fused with the polypeptide sequence at the 45-73 positions of *Neisseria meningitidis* pilin PiLE (NC_003112.2) and 6×His tag. The amino acid sequence of the optimized recombinant CTB fusion protein was set forth in SEQ ID NO: 6, wherein the 1-19 positions were the amino acid sequence of the DsbA signal peptide, the positions 20-122 were the amino acid sequence of the cholera toxin B subunit, the 128-156 positions were the amino acid sequence at the 45-73 position of *Neisseria meningitidis* PilE (NC_003112.2), the 157-166 positions were the flexible linker and the 6×His tag sequence; the coding sequence of the optimized recombinant CTB fusion protein was shown in SEQ ID NO: 5. The artificially synthesized gene encoding recombinant CTB fusion protein was digested with EcoR I and Hind III, and ligated into pMMB66EH expression vector (ATCC, ATCC37620) to construct pMMB66EH-rCTB4573 vector.

Sequencing results showed that the sequence shown in SEQ ID NO: 5 was inserted between the EcoR I and Hind III restriction sites of the pMMB66EH expression vector, indicating that the vector was correct.

2. Construction of $cld_{LT2}$ and pglL Tandem Expression Vectors

According to the amino acid sequence of the *Neisseria meningitidis* O-oligosaccharide transferase PglL (JN200826.1) published by GeneBank, its DNA sequence was synthesized by whole gene synthesis technique. The amino acid sequence of *Neisseria meningitidis* O-oligosaccharide transferase PglL was shown in SEQ ID NO: 8, and the gene encoding *Neisseria meningitidis* O-oligosaccharide transferase PglL was shown in SEQ ID NO: 7.

The artificially synthetized gene encoding PglL was digested with EcoR I and Hind III, ligated into pKK223-3 vector (commercially available from Uppasla Pharmacia LKB Biotechniligy AB, Sweden), and primers 223tac-box5' and 223tac-box3' were used for amplification to obtain the expression cassette of PglL, and ligated to the Bgl II site of pETtac28-$cld_{T2}$ obtained in Example 1, so as to construct the pETtac28-pglL-$cld_{LT2}$ recombinant expression vector. The primer sequences are as follows:

```
                                         (SEQ ID NO: 33)
223tac-box5': ATCGAGATCTACTGCATAATTCGTGTCGCTCAAG;

                                         (SEQ ID NO: 34)
223tac-box3': ATCGAGATCTGTCTCATGAGCGGATACATATTTG.
```

3. Construction of pglL Expression Vector

The expression cassette of pglL prepared in the above step 2 was ligated to the Bgl II site of pET28a (commercially available from Novagen) to construct a pETtac28-pglL recombinant expression vector.

4. Construction of *S. paratyphi* CMCC50973ΔcldΔwaaL/pMMB66EH-rEPA4573/pETtac28-pglL-$cld_{LT2}$ The pMMB66EH-rEPA4573 and pETtac28-pglL-$cld_{LT2}$ plasmids were electroporated orderly into the *S. paratyphi* CMCC50973ΔcldΔwaaL electroporation competent cells as prepared by the above methods, so as to construct the glycosylation engineering *Salmonella paratyphi* A *S. paratyphi* CMCC50973ΔcldΔwaaL/pMMB66EH-rEPA4573/pETtac28-pglL-$cld_{LT2}$.

5. Construction of *S. paratyphi* CMCC50973ΔwaaL/pMMB66EH-rEPA4573/pETtac28-pglL The pMMB66EH-rEPA4573 and pETtac28-pglL plasmids were electroporated orderly into the *S. paratyphi* CMCC50973ΔwaaL electroporation competent cells as prepared by the above methods, so as to construct the glycosylation engineering *Salmonella paratyphi* A *S. paratyphi* CMCC50973ΔwaaL/pMMB66EH-rEPA4573/pETtac28-pglL.

6. Construction of *S. paratyphi* CMCC50973ΔcldΔwaaL/pMMB66EH-rCTB4573/pETtac28-pglL-$cld_{LT2}$ The pMMB66EH-rCTB4573 and pETtac28-pglL-$cld_{LT2}$ plasmids were electroporated orderly into the *S. paratyphi*

CMCC50973ΔcldΔwaaL electroporation competent cells as prepared by the above methods, so as to construct the glycosylation engineering *Salmonella paratyphi* A *S. paratyphi* CMCC50973ΔcldΔwaaL/pMMB66EH-rCTB4573/pETtac28-pglL-cld$_{LT2}$.

7. Construction of *S. paratyphi* CMCC50973ΔwaaL/pMMB66EH-rCTB4573/pETtac28-pglL The pMMB66EH-rCTB4573 and pETtac28-pglL plasmids were electroporated orderly into the *S. paratyphi* CMCC50973ΔwaaL electroporation competent cells as prepared by the above methods, so as to construct the glycosylation engineering *Salmonella paratyphi* A *S. paratyphi* CMCC50973ΔwaaL/pMMB66EH-rCTB4573/pETtac28-pglL.

8. Construction of *S. paratyphi* CMCC50973ΔwaaL/pMMB66EH-rCTB4573

The pMMB66EH-rCTB4573 plasmid was electroporated orderly into the *S. paratyphi* CMCC50973ΔwaaL electroporation competent cells as prepared by the above methods, so as to construct the glycosylation engineering *Salmonella paratyphi* A *S. paratyphi* CMCC50973ΔwaaL/pMMB66EH-rCTB4573.

9. Construction of *S. paratyphi* CMCC50973ΔwaaL/pMMB66EH-rEPA4573

The pMMB66EH-rEPA4573 plasmid was electroporated orderly into the *S. paratyphi* CMCC50973ΔwaaL electroporation competent cells as prepared by the above methods, so as to construct the glycosylation engineering *Salmonella paratyphi* A *S. paratyphi* CMCC50973ΔwaaL/pMMB66EH-rEPA4573.

IV. Detection of Glycosylation Situation of rEPA4573 and rCTB4573

A single clone of glycosylation engineering bacteria was picked and inoculated into a LB medium containing ampicillin at a final concentration of 100 μg/mL and kanamycin at a final concentration of 50 μg/mL, cultured at 37° C. until $OD_{600}$ was about 0.6, and then IPTG was added at a final concentration of 1 mM, cooled to perform induction at 16° C. for 20 h.

On the next day, 1 mL of the bacterial liquor induced at 16° C. for 20 h was taken, centrifuged to take the bacteria, the bacteria were slowly suspended with 1× reduction buffer, treated with boiling water bath for 10 min, then subjected to SDS-PAGE electrophoresis. After electrophoresis was completed, the protein was transferred to a PVDF membrane by a Bio-Lab semi-dry transfer, the transfer was performed at constant voltage of 20V for 1 h, and anti-His mouse monoclonal antibody (commercially available from Sigma, Cat. A7058) was used for detection, in which specific procedures could be seen in the Molecular Cloning Guide.

Figure 3:
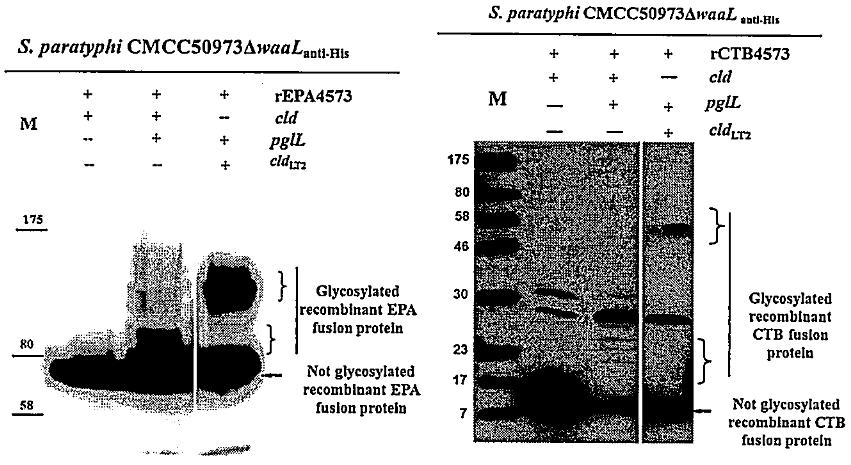
FIG. 3 shows a detection diagram of glycosylation modification of the recombinant fusion protein after the substitution of cld gene.

It can be seen from FIG. 3 that the molecular weights of the glycosylation-modified rEPA4573-OPS$_{Spty50973}$ and rCTB4573-OPS$_{Spty50973}$ were significantly increased after the cld gene of *S. paratyphi* CMCC50973 itself was replaced with cld$_{LT2}$, indicating that after the substitution of cld$_{LT2}$, the polysaccharide protein ratio of glycoprotein was significantly improved.

V. Increasing the Proportion of Polysaccharides in *Salmonella paratyphi* A O-Polysaccharide-Recombinant CTB Fusion Protein Via Tandem O-Glycosylation Sites 1. Construction of Recombinant CTB Fusion Protein (rCTB4573$_3$) Expression Vector Containing Three P1a Sequences In order to increase polysaccharide-protein ratio of glycoprotein, the present invention performed tandem fusion at C-terminus of CTB with 3 polypeptide sequences (P1a sequence) of the positions 45-73 of *Neisseria meningitidis* pilin PilE (NC_003112.2), i.e., rCTB4573$_3$ The amino acid sequence of the recombinant CTB fusion protein was shown in SEQ ID NO: 10, wherein the positions 1-19 were the amino acid sequence of the DsbA signal peptide; the positions 20-122 were the amino acid sequence of the cholera toxin B subunit; the positions 123-127 were the flexible linker; the positions 128-222 were the amino acid sequence of the 3 polypeptide sequences of the positions 45-73 of *Neisseria meningitidis* pilin PilE (NC_003112.2); the positions 223-232 were 6×His tag sequence; the coding sequence of the recombinant CTB fusion protein was shown in SEQ ID NO: 9. Wherein, the gene encoding the polypeptide as set forth in positions 45 to 73 of *Neisseria meningitidis* pilin PilE (NC_003112.2) was shown in SEQ ID NO: 14, and the protein sequence encoded by this gene was shown in SEQ ID NO: 13.

The artificially synthesized coding sequence of the recombinant CTB fusion protein was digested with EcoR I and Hind III, and ligated into pMMB66EH expression vector (ATCC, ATCC37620) to construct pMMB66EH-rCTB4573$_3$ vector.

The sequencing results showed that the sequence shown in SEQ ID NO: 9 was inserted between the EcoR I and Hind III restriction sites of the pMMB66EH expression vector, indicating that the vector was correct.

2. Construction of *S. paratyphi* CMCC50973ΔcldΔwaaL/pMMB66EH-rCTB4573$_3$/pETtac28-pglL-cld$_{LT2}$ The pMMB66EH-rCTB4573$_3$ and pETtac28-pglL-cld$_{LT2}$ plasmids were electroporated into the *S. paratyphi* CMCC50973ΔcldΔwaaL electroporation competent cells as prepared by the above methods, so as to construct the glycosylation engineering *S. paratyphi* CMCC50973ΔcldΔwaaL/pMMB66EH-rCTB4573$_3$/pETtac28-pglL-cld$_{LT2}$.

3. Preparation of rCTB4573$_3$-OPS$_{Spty50973}$

The method was the same as above mentioned.

Figure 4:
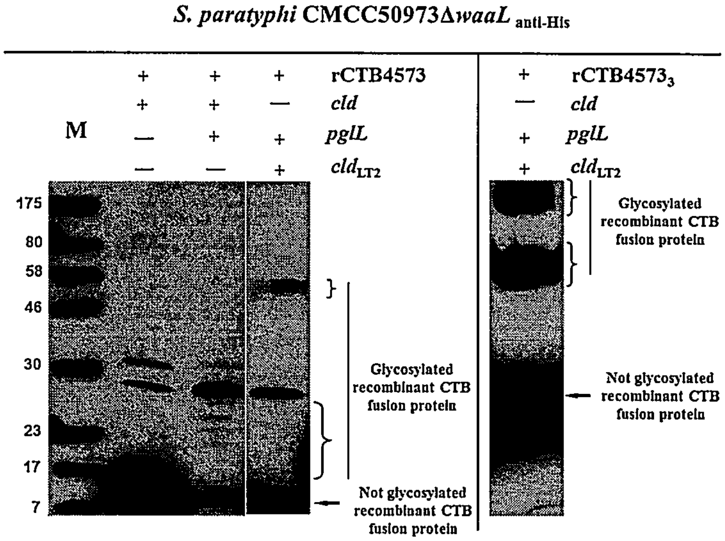
FIG. 4 shows a detection diagram of multi-site glycosylation modification of the recombinant CTB fusion proteins.

It can be seen from FIG. 4 that after the addition of three glycosylation sites, the recombinant CTB fusion protein underwent O-glycosylation modification, and at the same time, due to the addition of multiple glycosylation sites, the existence of multiple clusters of glycosylation strips indicated the multiple sites were all effective glycosylation sites.

VI. Acquisition of rEPA4573-OPS$_{Spty50973}$ and rCTB4573$_3$-OPS$_{Spty50973}$ 1. Purification of rEPA4573-OPS$_{Spty50973}$ Monoclones of the glycosylation engineering strain *S. paratyphi* CMCC50973ΔcldΔwaaL/pMMB66EH-rEPA4573/pETtac28-pglL-cld$_{LT2}$ were picked out, inoculated to a LB culture plate containing ampicillin and kanamycin double resistances, cultured at 37° C. until $OD_{600}$ reached about 0.6, then IPTG at a final concentration of 1 mM was added, and cooled to perform induction at 25° C. for 20 h.

1) Pre-Treatment of Samples 10 g of the above bacteria after induction at 25° C. for 20 h was taken, added with 100 mL of purified water, subjected to ultrasonication (ultrasonication for 3 s and suspension for 5 s, cumulative ultrasonication time 30 min), centrifuged at 12000 g of centrifugal force, and the supernatant was collected. To this crude extract, pH 7.5 Tris-HCL at a final concentration of 20 mM, NaCL at a final concentration of 0.2M and imidazole at a final concentration of 10 mM were added, fully stirred, then centrifuged again at 12000 g of centrifugal force, and the supernatant was collected and used as a crude extract containing the recombinant EPA fusion protein (rEPA4573-OPS$_{Spty50973}$) that was modified by *Salmonella paratyphi* A OPS.

2) Purifying Samples with Chelating Affinity Chromatographic Column

Chelating affinity chromatographic column (Φ1.6 cm*15 cm) was used for primary purification of samples. The column bed was first rinsed with 3 column bed volumes of 0.5M NaOH, then equilibrated with deionized water to neutral pH, then equilibrated with 3 column bed volumes of 0.5M $NiSO_4$, and then equilibrated with 1 column bed volume of B1 solution (20 mM pH 7.5 Tris-HCl, 0.5M NaCl, 500 mM imidazole), and finally equilibrated with 3 column bed volumes of A1 solution (20 mM pH 7.5 Tris-HCl, 0.5M NaCl, 10 mM imidazole), wherein the above-used flow rate was always 4 mL/min. The above crude extract containing rEPA4573-$OPS_{Spty50096}$ was loaded from A tube, and the unbound protein was washed off with solution A, and the elution was finally performed by using 100% B1 to collect 30 mL of eluate.

3) Desalting Samples

The sample that was preliminarily purified by the Chelating affinity chromatographic column was desalted by using G25 fine chromatographic column (Φ1.6 cm*30 cm), in which the mobile phase was A3 solution (20 mM pH 7.5 Tris-HCl). The column bed was firstly rinsed with 3 column bed volumes of 0.5M NaOH, then equilibrated with deionized water to pH neutral, and finally equilibrated with 3 column volumes of A3 solution. The sample was loaded from A tube, 60 mL of sample was collected, and the above-used flow rate was always 4 mL/min.

4) Further Purification of rEPA4573-$OPS_{Spty50973}$ by Using ProteinPak DEAE8HR Anion Exchange Chromatographic Column The desalted sample was further purified by ProteinPak DEAE8HR anion exchange chromatographic column (waters). The column bed was first rinsed with 3 column bed volumes of 0.5M NaOH, then equilibrated with deionized water to pH neutral, and then equilibrated with 3 column bed volumes of A3 solution (20 mM pH 7.5 Tris-HCl). The sample was loaded from A tube, the unbound glycoprotein was washed off with A3 solution, then linear elution was performed using 0-50% B3 solution (20 mM pH 7.5 Tris-HCl, 1M NaCl) for 30 min, and the eluate was collected, in which the above used flow rate was always 1 mL/min. The peak position of glycoprotein rEPA4573-$OPS_{Spty50973}$ was at position of about 8-18 mS/cm.

5) Fine Purification of rEPA4573-$OPS_{Spty50973}$ by Using Superdex 75 Chromatographic Column The sample as purified by ProteinPak DEAE8HR anion exchange chromatographic column was further purified by using Superdex 75 FPLC (Φ1:01 cm*30 cm, GE). The column bed was first washed with 3 column bed volumes of 0.5M NaOH, then equilibrated with deionized water to pH neutral, and then equilibrated with 3 column bed volumes of A4 solution (20 mM pH 7.5 PB, 0.9% NaCl). The sample in volume of 1 mL was loaded from a sample loop, and 8 to 11 mL of the effluent sample was collected, and this sample was the purified rEPA4573-$OPS_{Spty50973}$.

Figure 5:
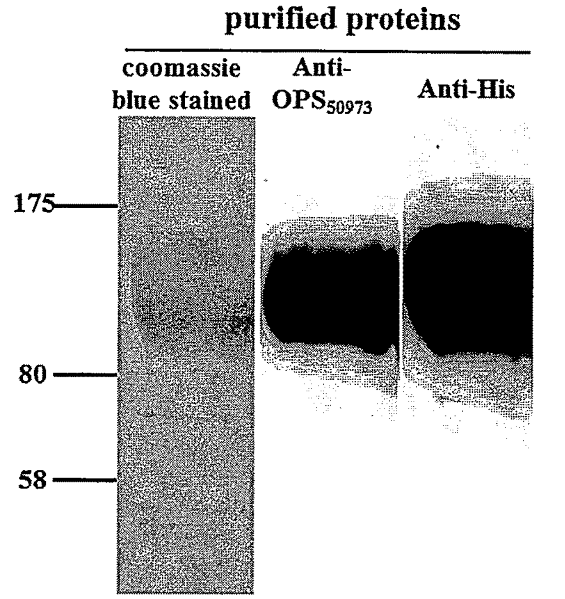
FIG. 5 shows a detection diagram of rEPA4573-OPS$_{Spty50973}$ purification effect.

This sample was analyzed by 8% SDS-PAGE and western blot, and the results were shown in FIG. 5.

2. Purification of $rCTB4573_3$-$OPS_{Spty50973}$

Monoclone of the glycosylation engineering strain *S. paratyphi* CMCC50973ΔcldΔwaaL/pMMB66EH-$rCTB4573_3$/pETtac28-pglL-$cld_{LT2}$ was picked out, inoculated to a LB culture medium with ampicillin and kanamycin double resistance, cultured at 37° C. until $OD_{600}$ was about 0.6, then IPTG at a final concentration of 1 mM was added, and cooled to perform induction at 16° C. for 20 h.

1) Pre-Treatment of Samples 10 g of the above bacteria after induction at 16° C. for 20 h was taken, added with 100 mL of purified water, subjected to ultrasonication (ultrasonication for 3 s and suspension for 5 s, cumulative ultrasonication time 30 min), centrifuged at 12000 g of centrifugal force, and the supernatant was collected. To this crude extract, pH 7.5 Tris-HCL at a final concentration of 20 mM, NaCL at a final concentration of 0.2M and imidazole at a final concentration of 10 mM were added, fully stirred, then centrifuged again at 12000 g of centrifugal force, and the supernatant was collected and used as a crude extract containing the recombinant CTB fusion protein ($rCTB4573_3$-$OPS_{Spty50973}$) that was modified by *Salmonella paratyphi* A O-polysaccharide.

2) Purifying Samples with Chelating Affinity Chromatographic Column

Chelating affinity chromatographic column (Φ1.6 cm*15 cm) was used for primary purification of samples. The column bed was first rinsed with 3 column bed volumes of 0.5M NaOH, then equilibrated with deionized water to neutral pH, then equilibrated with 3 column bed volumes of 0.5M $NiSO_4$, and then equilibrated with 1 column bed volume of B1 solution (20 mM pH 7.5 Tris-HCl, 0.5M NaCl, 500 mM imidazole), and finally equilibrated with 3 column bed volumes of A1 solution (20 mM pH 7.5 Tris-HCl, 0.5M NaCl, 10 mM imidazole), wherein the above-used flow rate was always 4 mL/min.

The above crude extract containing $rCTB4573_3$-$OPS_{Spty50973}$ was loaded from A tube, and the unbound protein was washed off with solution A, and the elution was finally performed by using 100% B1 to collect 30 mL of eluate.

3) Desalting Samples

The sample that was preliminarily purified by the Chelating affinity chromatographic column was desalted by using G25 fine chromatographic column (Φ1.6 cm*30 cm), in which the mobile phase was A2 solution (20 mM pH 5.4HAc—NaAc). The column bed was firstly rinsed with 3 column bed volumes of 0.5M NaOH, then equilibrated with deionized water to pH neutral, and finally equilibrated with 3 column volumes of A2 solution. The sample was loaded from A tube, 60 mL of sample was collected, and the above-used flow rate was always 4 mL/min.

Figure 6:
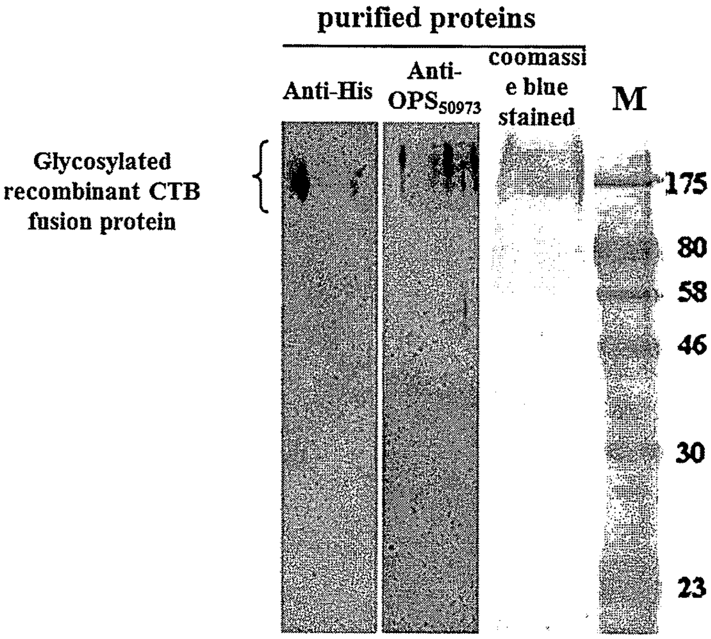
FIG. 6 shows a detection diagram of rCTB4573$_3$-OPS$_{Sp50973}$ purification effect.

4) Further Purification of $rCTB4573_3$-$OPS_{Spty50973}$ by Using ProteinPak SP8HR Cation Exchange Chromatographic Column The desalted sample was further purified by ProteinPak SP8HR cation exchange chromatographic column (waters). The column bed was first rinsed with 3 column bed volumes of 0.5M NaOH, then equilibrated with deionized water to pH neutral, and then equilibrated with 3 column bed volumes of A2 solution (20 mM pH5.4 HAc—NaAc). The sample was loaded from A tube, the unbound glycoprotein was washed off with A2 solution, then linear elution was performed using 0-50% B2 solution (20 mM pH5.4 HAc—NaAc, 1M NaCl) for 30 min, and the eluate was collected, in which the above used flow rate was always 1 mL/min. The peak position of glycoprotein $rCTB4573_3$-$OPS_{Sp50973}$ was at position of about 35-45 mS/cm. The sample was analyzed by 12% SDS-PAGE and western blot, and the results were shown in FIG. 6.

VII. Preparation and Animal Experimental Evaluation of Polysaccharide-Protein Conjugate Vaccines of $rCTB4573_3$-$OPS_{Spty50973}$ and rEPA4573-$OPS_{Spty50973}$ 1. Preparation of Polysaccharide-Protein Conjugate Vaccines of $rCTB4573_3$-$OPS_{Spty50973}$ and rEPA4573-$OPS_{Spty50973}$ The purified rCTB4573$_3$-OPS$_{Spty50973}$ and rEPA4573-OPS$_{Spty50973}$ were sterilized by filtration, and mixed with aluminum hydroxide adjuvant (Rehydragel LV, General Chemical) at a ratio of 9:1.

2. Preparation of O-Antigen (OPS$_{Spty50973}$)

LPS was firstly extracted by hot phenol-water method (SUN Yang, FENG Shuzhang, ZHU Lingwei, et al, "Preparation and identification of Enterohemorrhagic *Escherichia coli* O157 LPS monoclonal antibody, [J]. Journal of Zoonoses of China, 2007, 23 (10): 971-973), preserved by lyophilization, then dissolved with 1% glacial acetic acid at a concentration of 10 mg/ml, treated with boiling water bath for 90 minutes, then cooled to room temperature, and adjusted to pH 7.0. The supernatant was collected after centrifugation at 64,000×g for 5 hours, and thoroughly dialyzed with deionized water and preserved by lyophilization.

3. Animal Immunization and Effect Evaluation of Conjugate Vaccines of rCTB4573$_3$-OPS$_{Spty50973}$ and rEPA4573-OPS$_{Spty50973}$ 40 female Balb/c mice of 6 weeks old were randomly divided into 4 groups. Aluminum hydroxide, OPS$_{Spty50973}$, rCTB4573$_3$-OPS$_{Spty50973}$ and rEPA4573-OPS$_{Spty50973}$ samples were separately injected into muscles of the 4 group of mice, in which the aluminum hydroxide group was negative control, the other three groups were injected with 10 μg polysaccharide in an amount expressed in polysaccharide content; and blood samples were taken separately on the 1$^{st}$, 22$^{nd}$ and 50$^{th}$ day after immunization, and on the 10$^{th}$ day after the third immunization.

The antibody titer of anti-*Salmonella paratyphi* A O-polysaccharide in mice serum of each group was measured by indirect ELISA method. The enzyme-linked plate was coated with the extracted *Salmonella paratyphi* A LPS, in which each well was coated with 10 μg of LPS, and other procedures could be seen in "A Guide to Experimental Biomedical Biology".

Figure 7:
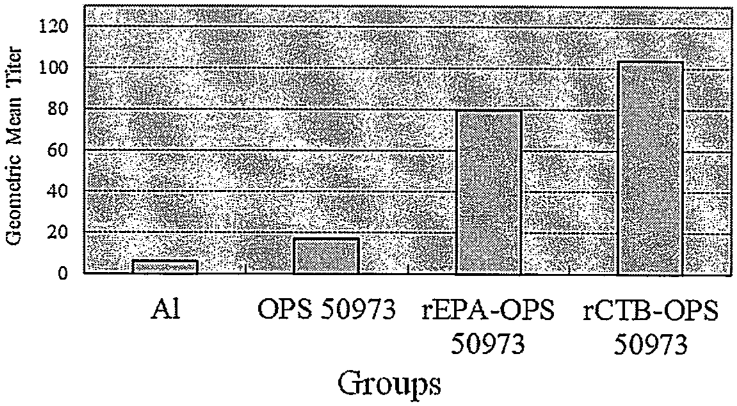
FIG. 7 shows an immunogenicity evaluation of glycoprotein conjugates.

It can be seen from FIG. 7, both of the rCTB4573$_3$-OPS$_{Spty50973}$ and rEPA4573-OPS$_{Spty50973}$ as prepared in the present invention via extending OPS of *Salmonella paratyphi* A CMCC50973 can induce mice to produce specific antibodies against *Salmonella paratyphi* A CMCC50973 OPS, in which the antibody titer increased significantly in comparison with the OPS group with injection of OPS only.

INDUSTRIAL APPLICATIONS

In comparison with Paratyphoid A polysaccharide-protein conjugate vaccines in the prior art, the present invention prepares Paratyphoid A polysaccharide-protein conjugate vaccines by using an O-antigen with extended carbohydrate chain by one-step bio-crosslinking method. The method comprises: using *Salmonella paratyphi* A as a host strain wherein the O-antigen chain length was extended and O-antigen ligase gene waaL was deleted, co-expressing a recombinant fusion protein gene and a *Neisseria meningitidis* O-oligosaccharide transferase gene pglL in the host strain, using the O-antigen of the host strain *Salmonella paratyphi* A to directly modify the recombinant fusion protein in manner of O-glycosylation modification, so as to obtain O-antigen-modified recombinant fusion protein of *Salmonella paratyphi* A and to prepare Paratyphoid A polysaccharide-protein conjugate vaccines rCTB4573$_3$-OPS$_{Spty50973}$ and rEPA4573-OPS$_{Spty50973}$. The results showed that the vaccines prepared by the present invention can induce in mice the generation of specific antibody against *Salmonella paratyphi* A CMCC50973 OPS, and the antibody titer is obviously improved in comparison with the mice with injection of OPS alone.

Unless otherwise indicated, all technical and scientific terms used herein have the same meaning as commonly understood by one of ordinary skill in the art to which this invention pertains. Exemplary methods and materials are described below. Although methods and materials similar or equivalent to those described in the text can also be used to carry out the present invention, they are obvious for those skilled in the art. All publications and other references mentioned herein are incorporated by reference in their entirety. In the event of inconsistencies, the present specification including definitions should prevail. All materials, methods and examples above mentioned are illustrative only and not restrictive.

What is claimed is:

1. A recombinant strain, which is obtained by introducing a $cld_{LT2}$ gene encoding an enzyme controlling chain length of O-antigen of *Salmonella typhimurium* into *Salmonella paratyphi* A which is deficient in cld gene encoding an enzyme controlling chain length of O-antigen;

wherein the amino acid sequence of the enzyme controlling chain length of the O-antigen of *Salmonella typhimurium* has the amino acid sequence as shown in SEQ ID NO: 2.

2. The recombinant strain according to claim 1, characterized in that the *Salmonella paratyphi* A which is deficient in cld gene encoding an enzyme controlling chain length of O-antigen is obtained by a method comprising the following steps:

(1) preparing a linear targeting DNA fragment 1, which has a nucleotide sequence as shown in SEQ ID NO: 11, and contains a cat gene;

(2) transforming pKD46 plasmid into a *Salmonella paratyphi* strain, to obtain a recombinant strain designated as *S. paratyphi*/pKD46;

(3) inducing expression of Red recombination system in the *S. paratyphi*/pKD46 strain, and transforming the linear targeting DNA fragment 1 into the *S. paratyphi*/pKD46 strain, so that the linear targeting DNA fragment 1 replaces the cld gene of the *S. paratyphi*/pKD46 strain to obtain a recombinant strain designated as *S. paratyphi* cld::cat/pKD46;

(4) deleting the pKD46 plasmid from the *S. paratyphi* cld::cat/pKD46 strain, to obtain a recombinant strain designated as *S. paratyphi* fcld::cat;

the *S. paratyphi* cld::cat is a *S. paratyphi* in which cld gene sequence is substituted with cat gene sequence;

(5) transforming plasmid pCP20 into the *S. paratyphi* cld::cat and deleting cat gene, to obtain a recombinant strain designated as *S. paratyphi* Δcld;

the *S. paratyphi* Δcld is a cld gene-deleted *S. paratyphi*.

3. The recombinant strain according to claim 1, wherein the gene encoding the enzyme controlling chain length of the O-antigen of *Salmonella typhimurium* has a sequence as shown in SEQ ID NO: 1.

* * * * *